United States Patent
Winter

(10) Patent No.: US 10,493,153 B2
(45) Date of Patent: Dec. 3, 2019

(54) ALKYLATED PHOTOREMOVABLE PROTECTING GROUPS AND USES THEREOF

(71) Applicant: Iowa State University Research Foundation, Inc., Ames, IA (US)

(72) Inventor: Arthur Henry Winter, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 0 days.

(21) Appl. No.: 16/140,218

(22) Filed: Sep. 24, 2018

(65) Prior Publication Data

US 2019/0231873 A1      Aug. 1, 2019

Related U.S. Application Data

(60) Provisional application No. 62/625,112, filed on Feb. 1, 2018.

(51) Int. Cl.
| | |
|---|---|
| *A61K 41/00* | (2006.01) |
| *C07F 5/02* | (2006.01) |
| *A61K 47/10* | (2017.01) |
| *A61K 47/22* | (2006.01) |

(52) U.S. Cl.
CPC .......... *A61K 41/0042* (2013.01); *A61K 47/10* (2013.01); *A61K 47/22* (2013.01); *C07F 5/02* (2013.01)

(58) Field of Classification Search
None
See application file for complete search history.

(56) References Cited

U.S. PATENT DOCUMENTS

| | | | |
|---|---|---|---|
| 9,957,498 B2 | 5/2018 | Winter et al. | |
| 2011/0081647 A1 | 4/2011 | Siddiqi et al. | |
| 2012/0009615 A1* | 1/2012 | Ulrich ................ | C07F 5/02 435/29 |
| 2016/0228845 A1 | 8/2016 | Winter et al. | |

FOREIGN PATENT DOCUMENTS

JP      2002169275      *   6/2002

OTHER PUBLICATIONS

IUPAC "Photochemistry" Compendium of Chemical Terminology, 2nd ed. (the "Gold Book"), https://doi.org/10.1351/goldbook. Feb. 24, 2014; version:2.3.3 (Year: 2014).*
Goswami ("BODIPY-Derived Photoremovable Protecting Groups Unmasked with Green Light" J. Am. Chem. Soc., vol. 137, 2015, p. 3783-3786) (Year: 2015).*
Rubinstein ("meso-Methylhydroxy BODIPY: a scaffold for photo-labile protecting groups" Chem. Commun. 2015, 51, p. 6369-6372) (Year: 2015).*
Wijesooriya ("A Photoactivatable BODIPY Probe for Localization-Based Super-Resolution Cellular Imaging" Angew. Chem. Int. Ed., 2018, 57, p. 12685-12689) (Year: 2018).*
Peterson ("Family of BODIPY Photocages Cleaved by Single Photons of Visible/Near-Infrared Light" J. Am. Chem. Soc., 2018, 140, p. 7343-7346) (Year: 2018).*
European Medicines Agency (downloaded from https://www.ema.europa.eu/en/documents/scientific-guideline/questions-answers-ethanol-context-revision-guideline-excipients-label-package-leaflet-medicinal_en.pdf on May 28, 2019, p. 1-14, 2014) (Year: 2014).*
Loudet ("BODIPY Dyes and Their Derivatives: Syntheses and Spectroscopic Properties" Chem. Rev. 2007, 107, p. 4891-1932) (Year: 2007).*
"U.S. Appl. No. 15/016,467, Restriction Requirement dated Dec. 15, 2016", 11 pgs.
"U.S. Appl. No. 15/016,467, Response filed Feb. 9, 2016 to Restriction Requirement dated Dec. 15, 2016", 8 pgs.
"U.S. Appl. No. 15/016,467, Non Final Office Action dated Apr. 7, 2017", 9 pgs.
"U.S. Appl. No. 15/016,467, Response filed Jun. 7, 2017 to Non Final Office Action dated Apr. 7, 2017", 8 pgs.
"U.S. Appl. No. 15/016,467, Non Final Office Action dated Sep. 20, 2017", 6 pgs.
"U.S. Appl. No. 15/016,467, Response filed Oct. 31, 2017 to Non Final Office Action dated Sep. 20, 2017", 7 pgs.
"U.S. Appl. No. 15/016,467, Notice of Allowance dated Jan. 18, 2018", 10 pgs.
"U.S. Appl. No. 15/016,467, Corrected Notice of Allowance dated Feb. 9, 2018", 5 pgs.
Klan, P., et al., "Photoremovable Protecting Groups in Chemistry and Biology: Reaction Mechanisms and Efficacy", Chemical Reviews, 113, (2013), 119-191.
Salanina, T., et al., "In Search of the Perfect Photocage: Structure—Reactivity Relationships in meso-Methyl BODIPY Photoremovable Protecting Groups", J. Am. Chem. Soc., 139, (2017), 15168-15175.
Yu, H., et al., "Chemistry and biological applications of photo-labile organic molecules", Chemical Society Reviews, 39(2), (2010), 464-473.

* cited by examiner

*Primary Examiner* — Amy C Bonaparte
(74) *Attorney, Agent, or Firm* — Schwegman Lundberg & Woessner, P.A.

(57) ABSTRACT

The invention relates to a method for photoreleasing a moiety G from a compound of the formula A-G. The methods of the present invention comprise irradiating a composition comprising the compound of the formula A-G at a wavelength of >500 nm, so as to photorelease the moiety G from the moiety A; wherein the moiety A comprises a chromophore and the moiety G comprises an organic compound.

26 Claims, No Drawings

ALKYLATED PHOTOREMOVABLE PROTECTING GROUPS AND USES THEREOF

This application claims the benefit of U.S. Serial Appl. Ser. No. 62/625,112, filed Feb. 1, 2018, which is incorporated by reference as if fully set forth herein.

STATEMENT OF GOVERNMENT SUPPORT

This invention was made with government support under grants DE-SC0014038 and CHE1464956 awarded by the U.S. Department of Energy and the National Science Foundation, respectively. The government has certain rights in the invention.

BACKGROUND

Photoremovable protecting groups, sometimes called "photocages" or "phototriggers," are light-sensitive chemical moieties that mask substrates through covalent linkages that render the substrates inert. Upon irradiation, the substrates are released, restoring their reactivity or function. While photocages have important applications in areas such as organic synthesis, photolithography, and light-responsive organic materials, these structures are particularly prized for their ability to trigger biological activity with high spatial and temporal resolution. Examples of such chemical tools include photocaged proteins, nucleotides, ions, neurotransmitters, pharmaceuticals, fluorescent dyes, and small molecules (e.g., caged ATP). These biologically relevant caged molecules and ions can be released from the caging structure within particular biological microenvironments using pulses of focused light. The most popular photocages used in biological studies are the o-nitrobenzyl systems and their derivatives, but other photocages that see significant use include those based on the phenacyl, acridinyl, benzoinyl, coumarinyl, and o-hydroxynaphthyl structures. Unfortunately, a significant limitation of these photocages is that they absorb mostly in the ultraviolet (UV), where the limited penetration of UV light into tissues largely restricts these studies to fixed cells and tissue slices. Furthermore, prolonged exposure of cells or tissues to intense UV light can lead to cellular damage or death. Consequently, new photocaging structures that absorb visible light are needed.

SUMMARY

Embodiments of the present invention relate to photoremovable groups that are photoremovable at wavelengths of light greater than 500 nm.

DESCRIPTION

Reference will now be made in detail to embodiments of the present invention, examples of which are illustrated in part in the accompanying drawings. While the disclosed embodiments of the present invention will be described in conjunction with the enumerated claims, it will be understood that the exemplified embodiments of the present invention are not intended to limit the claims to the disclosed embodiments.

Embodiments of the present invention relate to compounds of the formula A-G, wherein:
G can be any organic or inorganic compound that can be photoreleasably linked directly or indirectly by any suitable means (e.g., covalently via ether, amine, ester, amide or carbamate linkages, or the like) to the moiety A; and
A is of formula I:

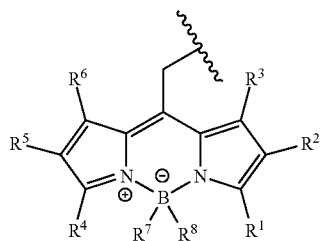

and salts thereof;
wherein:
the wavy line represents the attachment point of the moiety A to the moiety G; $R^1$, $R^2$, $R^3$, $R^4$, $R^5$, and $R^6$ are each, independently, hydrogen, halogen, optionally substituted $C_1$-$C_6$-alkyl, optionally substituted $C_2$-$C_6$-alkenyl or ($C_6$-$C_{14}$-aryl)-($C_2$-$C_6$-alkenyl-), wherein the ($C_6$-$C_{14}$-aryl)-($C_2$-$C_6$-alkenyl-) is optionally substituted on the $C_2$-$C_6$-alkenyl or the $C_6$-$C_{14}$-aryl; and $R^7$ and $R^8$ are each, independently, optionally substituted $C_1$-$C_6$-alkyl, optionally substituted $C_2$-$C_6$-alkenyl or optionally substituted $C_6$-$C_{14}$-aryl. In some embodiments, $R^1$, $R^2$, $R^3$, $R^4$, $R^5$, and $R^6$ are each, independently, hydrogen, halogen, optionally substituted $C_1$-$C_6$-alkyl, optionally substituted $C_2$-$C_6$-alkenyl or ($C_6$-$C_{14}$-aryl)-($C_2$-$C_6$-alkenyl-), wherein the ($C_6$-$C_{14}$-aryl)-($C_2$-$C_8$-alkenyl-) is optionally substituted on the $C_2$-$C_8$-alkenyl or the $C_8$-$C_{14}$-aryl or optionally substituted ($C_2$-$C_8$-heterocyclyl-); and $R^7$ and $R^8$ are each, independently, optionally substituted $C_1$-$C_8$-alkyl or optionally substituted $C_8$-$C_{14}$-aryl.

Embodiments of the present invention relate to compounds of the formula A-G, wherein:
G can be any organic or inorganic compound that can be photoreleasably linked directly or indirectly by any suitable means (e.g., covalently via ether, amine, ester, amide or carbamate linkages, or the like) to the moiety A; and
A is of formula II:

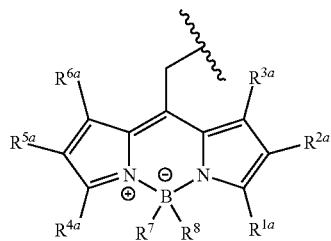

and salts thereof,
wherein:
the wavy line represents the attachment point of the moiety A to the moiety G; $R^{1a}$, $R^{2a}$, $R^{3a}$, $R^{4a}$, $R^{5a}$, and $R^{6a}$ are each, independently, hydrogen, acyl (e.g., acetyl $CH_3C(O)$—), carboxy, optionally substituted $C_1$-$C_8$-alkyl, optionally substituted $C_1$-$C_8$-alkoxy, amino, optionally substituted $C_2$-$C_8$-alkenyl, optionally substituted $C_8$-$C_{14}$-aryl, optionally substituted $C_2$-$C_3$-heteracylyl, optionally substituted $C_2$-$C_3$-heterocycly-($C_2$-$C_8$-alkenyl-), wherein the ($C_2$-$C_3$- heterocyclyl)-(C$_2$-C$_8$-alkenyl-) is optionally substituted on the C$_2$-C$_8$-alkenyl or the C$_2$-C$_8$-heterocyclyl, or R$^{1a}$ and R$^{2a}$, R$^{2a}$ and R$^{3a}$, R$^{4a}$ and R$^{5a}$ or R$^{5a}$ and R$^{6a}$, together with the carbon atoms to which they are attached, form an optionally substituted C$_2$-C$_8$-heterocyclyl or an optionally substituted C$_8$-C$_{14}$-aryl: and R$^7$ and R$^8$ are each, independently, optionally substituted C$_1$-C$_8$-alkyl, optionally substituted C$_2$-C$_8$-alkenyl or optionally substituted C$_8$-C$_{14}$-aryl.

Compounds of the formula A-G comprising the moiety A have significant advantages over known photoremovable groups at least because: (i) they can be removed by irradiating at a wavelength of >500 nm; (ii) ease of their synthesis; (iii) the BODIPY chromophore is biocompatible (Choyke et al., *Mol. Imaging* 8: 1536 (2009)); and the compounds A-G comprising have excellent optical properties (e.g., high extinction coefficients $4.0 \times 10^4$ $M^{-1}cm^{-1}$ to about $8.0 \times 10^4$ $M^{-1}cm^{-1}$). In sum, A can replace known photoremovable groups, such as the o-nitrobenzyl photoremovable groups, and can be used as protecting groups for any moiety G for which known photoremovable groups have previously been used to protect including nucelotides, peptides, proteins, carboxylates (e.g., acetic acid; gamma aminobutyric acid; N-methyl-D-aspartate; arachidonic acid; and lipids); amines, amides, alcohols, phenols, phosphates, ions (e.g., Ca$^{2+}$); and fluorophores/dyes (e.g., 7-hydroxycoumarins, pyrones; and rhodamines). See Petr Klán et al., *Chem. Rev.* 113: 119-191 (2013); and Dynamic Studies in Biology 5-20 (Maurice Goeldner and Richard Givens eds., Wiley VCH Verlag GmbH & Co. KGaA 2005), both of which are incorporated by reference as if fully set forth herein.

As used herein, the term "salts" refer to derivatives of the disclosed compounds wherein the parent compound is modified by making acid or base salts thereof. Examples of salts include, but are not limited to, mineral or organic acid salts of basic groups such as amines; and alkali or organic salts of acidic groups such as carboxylic acids. For example, salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The term "acyl" as used herein refers to a group containing a carbonyl moiety wherein the group is bonded via the carbonyl carbon atom. The carbonyl carbon atom is also bonded to another carbon atom, which can be part of a substituted or unsubstituted alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-40, 6-10, 1-5 or 2-5 additional carbon atoms bonded to the carbonyl group. An acryloyl group is an example of an acyl group. An acyl group can also include heteroatoms within the meaning here. A nicotinoyl group (pyridyl-3-carbonyl) is an example of an acyl group within the meaning herein. Other examples include acetyl, benzoyl, phenylacetyl, pyridylacetyl, cinnarnoyl, and acryloyl groups and the like. When the group containing the carbon atom that is bonded to the carbonyl carbon atom contains a halogen, the group is termed a "haloacyl" group. An example is a trifluoroacetyl group.

The term "amine" and "amino" as used herein refers to a substituent of the form —NH$_2$, —NHR, —NR$_2$, —NR$_3^+$, wherein each R is independently selected, and protonated forms of each, except for —NR$_3^+$, which cannot be protonated. Accordingly, any compound substituted with an amino group can be viewed as an amine. An "amino group" within the meaning herein can be a primary, secondary, tertiary, or quaternary amino group. An "alkylamino" group includes a monoalkylamino, dialkylamino, and trialkylamino group.

As used herein, the term "C$_{1-6}$-alkyl" refers to monovalent saturated aliphatic hydrocarbyl groups having from 1 to 6 carbon atoms, where the group can be substituted or unsubstituted. This term includes, but is not limited to, linear and branched hydrocarbyl groups such as methyl (CH$_3$—), ethyl (CH$_3$CH$_2$—), n-propyl (CH$_3$CH$_2$CH$_2$—), isopropyl ((CH$_3$)$_2$CH—), n-butyl (CH$_3$CH$_2$CH$_2$CH$_2$—), isobutyl ((CH$_3$)$_2$CHCH$_2$—), sec-butyl ((CH$_3$)(CH$_3$CH$_2$)CH—), t-butyl ((CH$_3$)$_3$C—), n-pentyl (CH$_3$CH$_2$CH$_2$CH$_2$CH$_2$—), and neopentyl ((CH$_3$)$_3$CCH$_2$—). The term C$_{1-6}$-alkyl also includes cycloalkyl groups including, but not limited to, cyclopropyl, cyclobutyl, cyclopentyl, and cyclohexyl.

The term "C$_1$-C$_{20}$-alkylenyl" as used herein refers to straight chain and branched, saturated divalent groups having from 1 to 20 carbon atoms, 10 to 20 carbon atoms, 12 to 18 carbon atoms, 1 to about 20 carbon atoms, 1 to 10 carbons, 1 to 8 carbon atoms, 1 to 6 carbon atoms or 2 to 4 carbon atoms, where the group can be substituted or unsubstituted. Examples of straight chain C$_1$-C$_{20}$-alkylenyl groups include those with from 1 to 6 carbon atoms such as —CH$_2$—, —CH$_2$CH$_2$—, —CH$_2$CH$_2$CH$_2$—, —CH$_2$CH$_2$CH$_2$CH$_2$—, and —CH$_2$CH$_2$CH$_2$CH$_2$CH$_2$—. Examples of branched (C$_1$-C$_{20}$)-alkylenyl groups include —CH(CH$_3$)CH$_2$— and —CH$_2$CH(CH$_3$)CH$_2$—.

As used herein, the term "C$_{2-6}$-alkenyl" refers to monovalent and divalent unsaturated hydrocarbyl groups having from 2 to 6 carbon atoms, where the group can be substituted or unsubstituted. This term includes, but is not limited to, linear and branched hydrocarbyl groups such as vinyl (CH$_2$=CH—), propenyl (CH$_2$=CH$_2$CH$_2$—), isopropenyl ((CH$_3$)(CH$_2$)C—), —CH=CH—, —CH=CH—CH$_2$—, —CH=CH—CH=CH—, and the like. The term C$_{2-6}$-alkenyl also includes cycloalkenyl groups including, but not limited to, cyclopentenyl and cyclohexenyl.

As used herein, the term "C$_6$-C$_{14}$-aryl" refers to cyclic aromatic hydrocarbons having from 6 to 14 carbon atoms (e.g., 6 to 12 carbon atoms or 6 to 10 carbon atoms), where the group can be substituted or unsubstituted. Such aryl groups may be substituted or unsubstituted. Aryl groups include, but are not limited to, phenyl, biphenyl, fluorenyl, phenanthrenyl, and naphthyl groups.

As used herein, the term "C$_2$-C$_8$-heterocyclyl" refers to cyclic aromatic or non-aromatic hydrocarbons having from 2 to 8 carbon atoms (e.g., 3 to 5 carbon atoms) and one or more heteroatoms such as nitrogen, oxygen or sulfur, where the group can be substituted or unsubstituted. Such heterocyclyl groups may be monocyclic or fused bycyclic and can be substituted or unsubstituted. Heterocyclyl groups include, but are not limited to, pyridinyl, pyrimidinyl, pyrazinyl, triazinyl, quinolinyl, quinazolinyl, quinoxalinyl, furanyl, thiophenyl, pyrrolyl, pyrazolyl, imidazolyl, oxazolyl, thiazolyl, isoxazolyl, isothiazolyl, oxadiazolyl, thiadiazolyl, triazolyl, benzimidazolyl, benzoxazolyl, benzthiazolyl, benzisoxazolyl, benzisothiazolyl, piperidynyl, piperazinyl, morpholinyl, pyrrolidinyl, tetrahydrofuranyl, and the like.

"Substituted" as used throughout the specification refers broadly to replacement of one or more of the hydrogen atoms of a group (e.g., C$_{1-6}$-alkyl, C$_{2-6}$-alkenyl, C$_6$-C$_{14}$-aryl, and C$_2$-C$_6$-heterocyclyl) with substituents known to those skilled in the art and resulting in a stable compound as described herein. Examples of suitable substituents include, but are not limited to, alkyl (e.g., $C_{1-6}$-alkyl), alkenyl (e.g., $C_{2-6}$-alkenyl), aryl (e.g., $C_6$-$C_{14}$-aryl), alkaryl (e.g., $C_{1-6}$-alkyl-$C_6$-$C_{14}$-aryl), hydroxy, alkoxy (e.g., $C_{1-6}$-alkyl-O—), aryloxy (e.g., $C_6$-$C_{14}$-aryl-O—), carboxy (e.g., $CO_2H$ or $CO_2^-X^+$, where $X^+$ is a suitable counterion, such as a sodium or potassium cation), alkylcarboxy (e.g., $C_{1-6}$-alkyl-C(O)O—), arylcarboxy (e.g., $C_6$-$C_{14}$-aryl-C(O)O—), alkyloxycarbonyl (e.g., —C(O)O—$C_{1-6}$-alkyl), aryloxycarbonyl (e.g., —C(O)O—$C_6$-$C_{14}$-aryl), cyano, cyanate ester (i.e., an —OCN group), silyl, siloxyl, phosphine, halogen (e.g., F, Cl, Br, and I), nitro, and $C_2$-$C_6$-heterocyclyl-. Other suitable substituents include amino groups of the formula —N(R$^8$)$_2$, wherein each R$^8$ is hydrogen, alkyl (e.g., $C_{1-6}$-alkyl), aryl (e.g., $C_6$-$C_{14}$-aryl) or alkaryl (e.g., $C_{1-6}$-alkyl-$C_6$-$C_{14}$-aryl), wherein each alkyl, aryl or alkaryl can be substituted; and —[O—R$^9$—]$_p$O—R$^{10}$, wherein R$^9$ is alkylenyl (e.g., $C_1$-$C_{20}$-alkylenyl) or cycloalkylenyl (e.g., ($C_3$-$C_{20}$)-cycloalkylenyl), R$^{10}$ is alkyl (e.g., $C_{1-6}$-alkyl), and p is an integer from 1 to about 10 (e.g., an integer from 1 to 5, 2 to 8, 2 to 5 or 2 to 4).

R$^1$ and R$^4$ in the moiety A, can each be, independently, an optionally substituted $C_1$-$C_6$-alkyl. R$^1$ and R$^4$ can each be methyl.

R$^3$ and R$^6$ in the moiety A, can each be, independently, an optionally substituted $C_1$-$C_6$-alkyl. R$^3$ and R$^6$ can each be methyl.

R$^{3a}$ and R$^{6a}$ in the moiety A, can each be, independently, an optionally substituted $C_1$-$C_6$-alkyl. R$^{3a}$ and R$^{6a}$ can each be methyl.

R$^1$, R$^3$, R$^4$, and R$^6$ in the moiety A, can each be, independently, an optionally substituted $C_1$-$C_6$-alkyl. For example, R$^1$, R$^3$, R$^4$, and R$^6$ in the moiety A can each be methyl.

R$^2$ and R$^5$ can each be, independently, halogen. R$^2$ and R$^5$ can each be, independently, fluorine, chlorine, bromine, iodine or combinations thereof. R$^2$ and R$^5$ can each be, independently, chlorine, bromine, iodine or combinations thereof. R$^2$ and R$^5$ can each be chlorine, bromine or iodine. R$^2$ and R$^5$ can each be iodine. R$^2$ and R$^5$ can each be, independently, halogen and R$^1$, R$^3$, R$^4$, and R$^6$ can each be, independently, an optionally substituted $C_1$-$C_6$-alkyl. R$^2$ and R$^5$ can each be, independently, halogen and R$^1$, R$^3$, R$^4$, and R$^6$ are each methyl. R$^2$ and R$^5$ can each be, independently, chlorine, bromine or iodine and R$^1$, R$^3$, R$^4$, and R$^6$ are each methyl. R$^2$ and R$^5$ can each be iodine and R$^1$, R$^3$, R$^4$, and R$^6$ are each methyl.

At least one of R$^{1a}$, R$^{3a}$, R$^{4a}$, and R$^{6a}$ can be $C_2$-$C_8$-heterocycly-($C_2$-$C_6$-alkenyl-). In some instances, two of R$^{1a}$, R$^{3a}$, R$^{4a}$, and R$^{6a}$ can be $C_2$-$C_8$-heterocycly-($C_2$-$C_6$-alkenyl-). In some instances, three of R$^{1a}$, R$^{3a}$, R$^{4a}$, and R$^{6a}$ can be $C_2$-$C_8$-heterocycly-($C_2$-$C_6$-alkenyl-). And in some instances, each of R$_{1a}$, R$_{3a}$, R$_{4a}$, and R$^{6a}$ can be $C_2$-$C_3$-heteracycly-($C_2$-$C_6$-alkenyl-).

At least one of R$^{1a}$ and R$^{4a}$ can be $C_2$-$C_8$-heterocycly. In some instances, two of R$^{1a}$ and R$^{4a}$ can be.

R$^7$ and R$^8$ can each be, independently, optionally substituted $C_1$-$C_6$-alkyl or optionally substituted $C_6$-$C_{14}$-aryl. For example, R$^7$ and R$^8$ can each be, independently, methyl or phenyl. R$^7$ and R$^8$ can each be methyl. R$^7$ and R$^8$ can each be phenyl. R$^7$ and R$^8$ can each be, independently, optionally substituted $C_1$-$C_6$-alkyl or optionally substituted $C_6$-$C_{14}$-aryl; R$^2$ and R$^5$ can each be, independently, halogen; and R$^1$, R$^3$, R$^4$, and R$^6$ can each be, independently, an optionally substituted $C_1$-$C_6$-alkyl. R$^7$ and R$^8$ can each be, independently, optionally substituted $C_1$-$C_6$-alkyl; R$^2$ and R$^5$ can each be, independently, halogen; and R$^1$, R$^3$, R$^4$, and R$^8$ can each be, independently, an optionally substituted $C_1$-$C_6$-alkyl. R$^7$ and R$^8$ can each be, independently, optionally substituted $C_6$-$C_{14}$-aryl; R$^2$ and R$^5$ can each be, independently, halogen; and R$^1$, R$^3$, R$^4$, and R$^6$ can each be, independently, an optionally substituted $C_1$-$C_6$-alkyl. R$^7$ and R$^8$ can each be methyl or phenyl; R$^2$ and R$^5$ can each be, independently, halogen; and R$^1$, R$^3$, R$^4$, and R$^6$ can each be, independently, an optionally substituted $C_1$-$C_6$-alkyl. R$^7$ and R$^8$ can each be methyl or phenyl; R$^2$ and R$^5$ can each be, independently, chlorine, bromine or iodine; and R$^1$, R$^3$, R$^4$, and R$^6$ can each be, independently, an optionally substituted $C_1$-$C_6$-alkyl. R$^7$ and R$^8$ can each be methyl or phenyl; R$^2$ and R$^5$ can each be, independently, chlorine, bromine or iodine; and R$^1$, R$^3$, R$^4$, and R$^6$ can each be methyl. R$^7$ and R$^8$ can each be methyl or phenyl; R$^2$ and R$^5$ can each be iodine; and R$^1$, R$^3$, R$^4$, and R$^6$ can each be methyl. R$^7$ and R$^8$ can each be methyl; R$^2$ and R$^5$ can each be iodine; and R$^1$, R$^3$, R$^4$, and R$^6$ can each be methyl. R$^1$ and R$^8$ can each be phenyl; R$^2$ and R$^5$ can each be iodine; and R$^1$, R$^3$, R$^4$, and R$^6$ can each be methyl.

In some embodiments, the moiety A is a moiety of the formula:

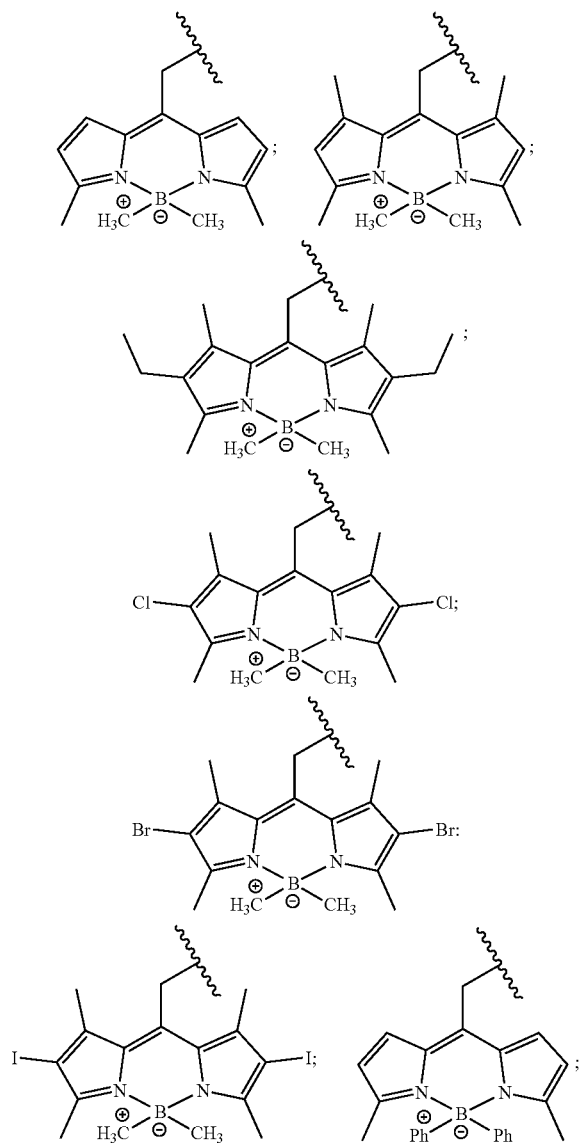

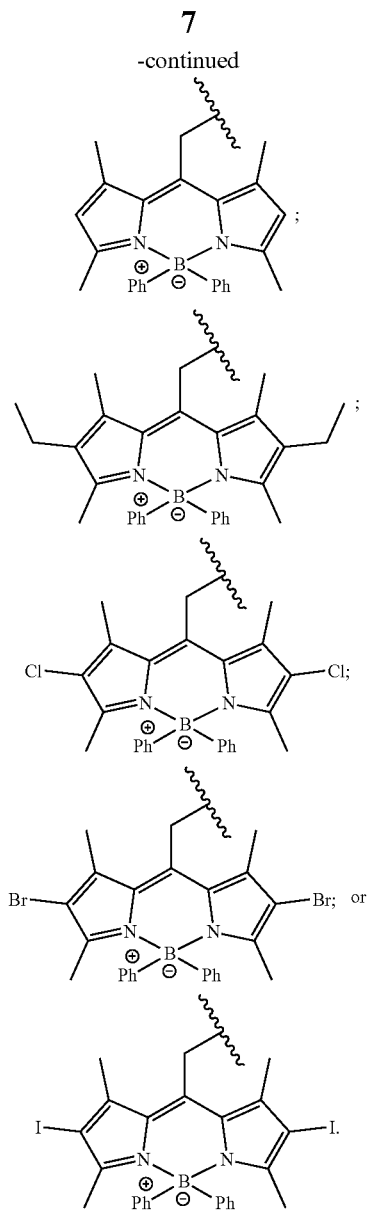
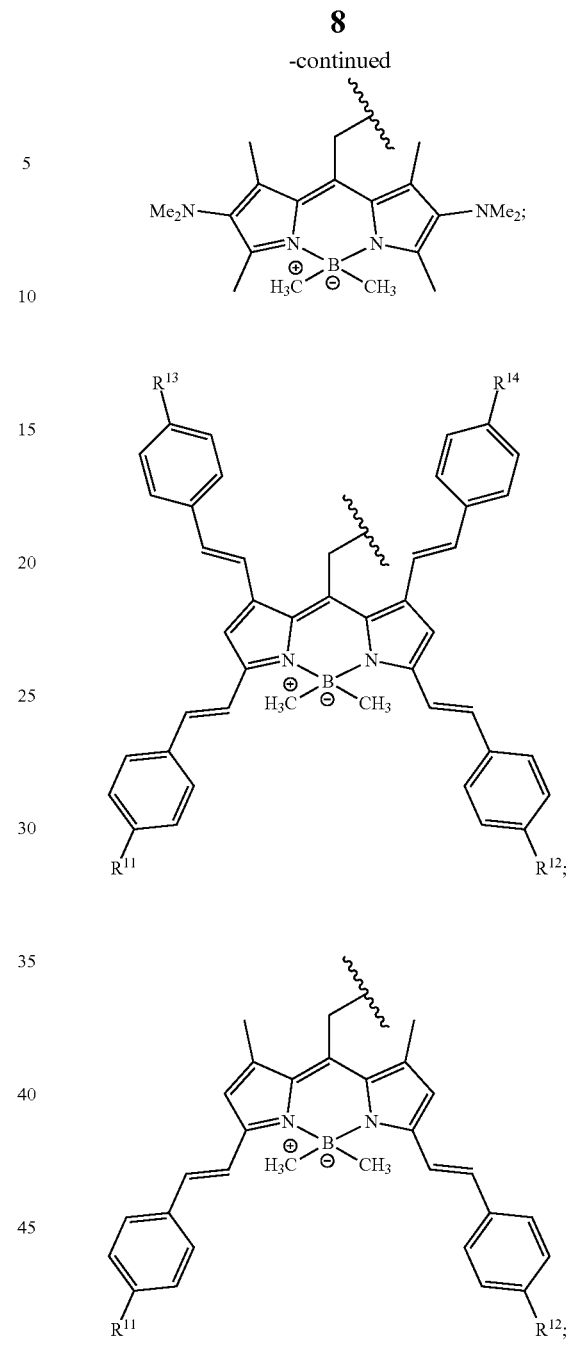
The moiety A can also be a moiety of the formula:
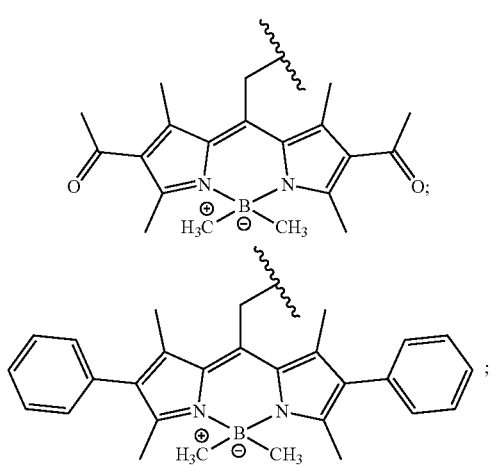
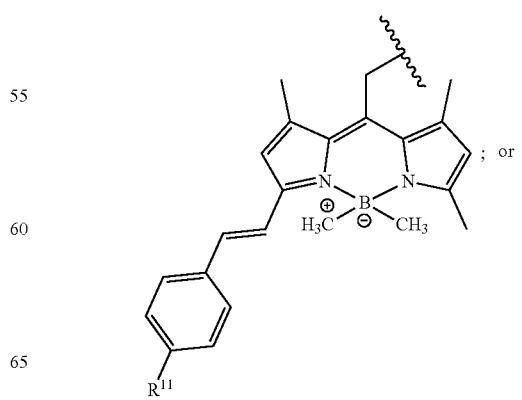

-continued

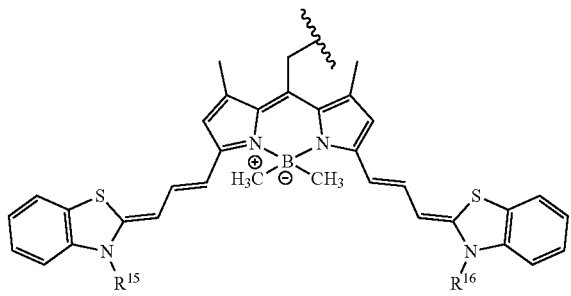

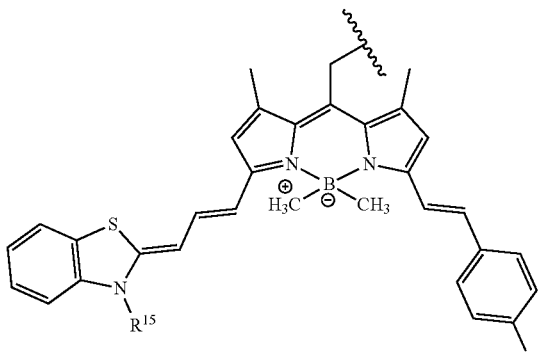

wherein $R^{11}$-$R^{14}$ are each independently H, halo, nitro, cyano, acyl, $C_1$-$C_6$-alkyl, $C_1$-$C_6$-alkoxy, amino or —[O—$R^9$—]$_p$O—$R^{10}$, wherein $R^9$ is alkylenyl (e.g., $C_1$-$C_{20}$-alkylenyl) or cycloalkylenyl (e.g., ($C_3$-$C_{20}$)-cycloalkylenyl), $R^{10}$ is alkyl (e.g., $C_{1-6}$-alkyl), and p is an integer from 1 to about 10 (e.g., an integer from 1 to 5, 2 to 8, 2 to 5 or 2 to 4); and $R^{15}$ and $R^{16}$ are each H or $C_1$-$C_6$-alkyl.

The following A-groups can be considered "push-pull" derivatives, because they contain electron donating groups (e.g., dimethylamino) on one side of the A-group and electron withdrawing group on another side of the A-group.

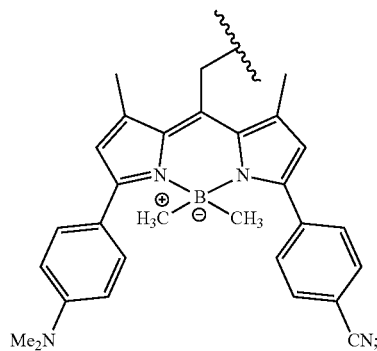

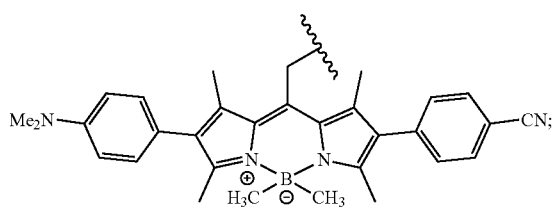

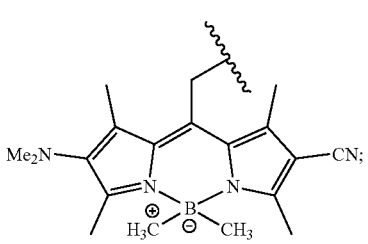

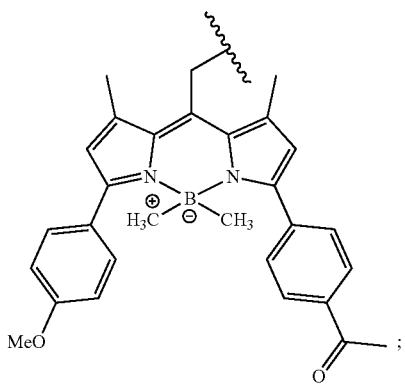

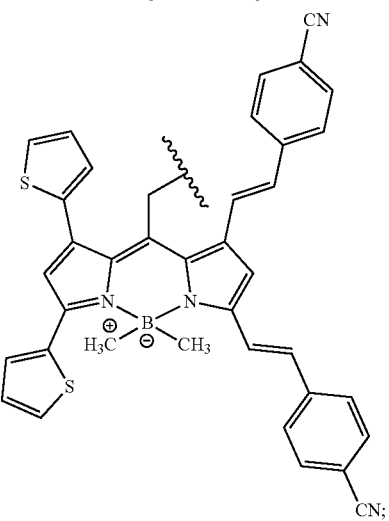

11
-continued
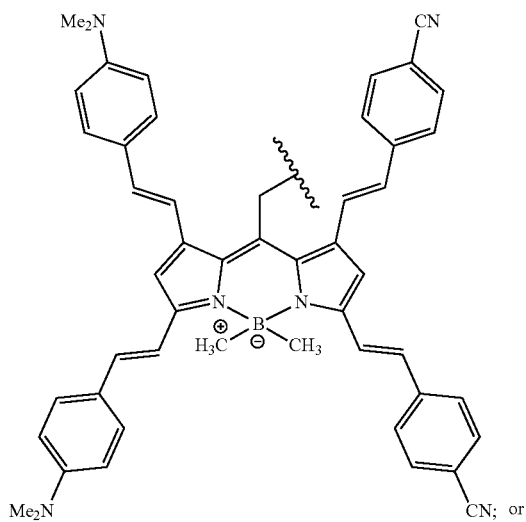
12
-continued
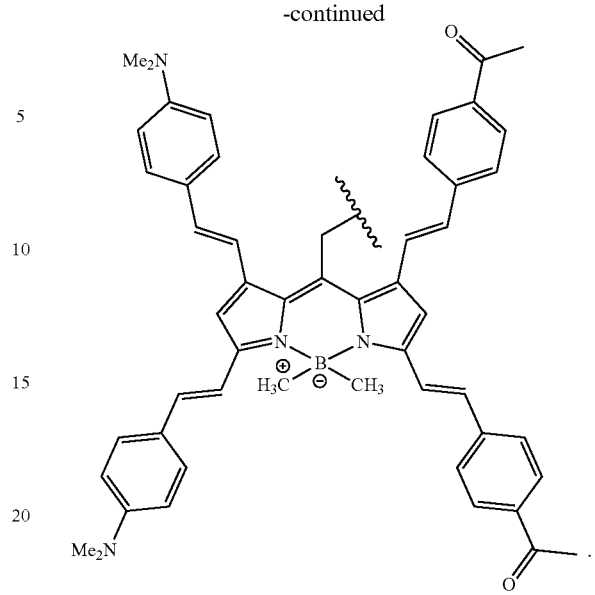
The following A-groups are also within the scope of the instant disclosure:
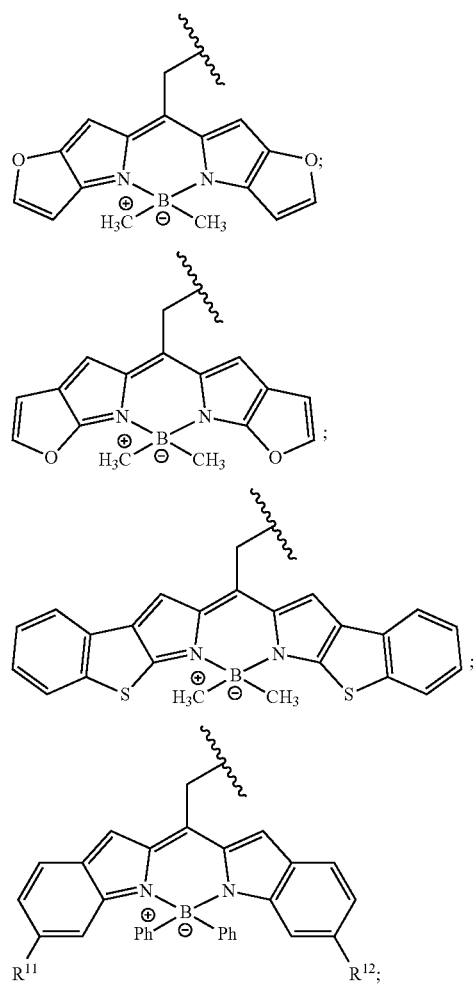
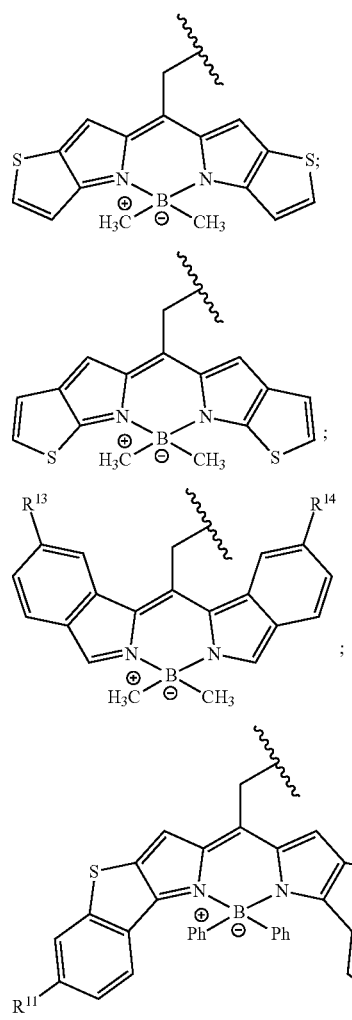

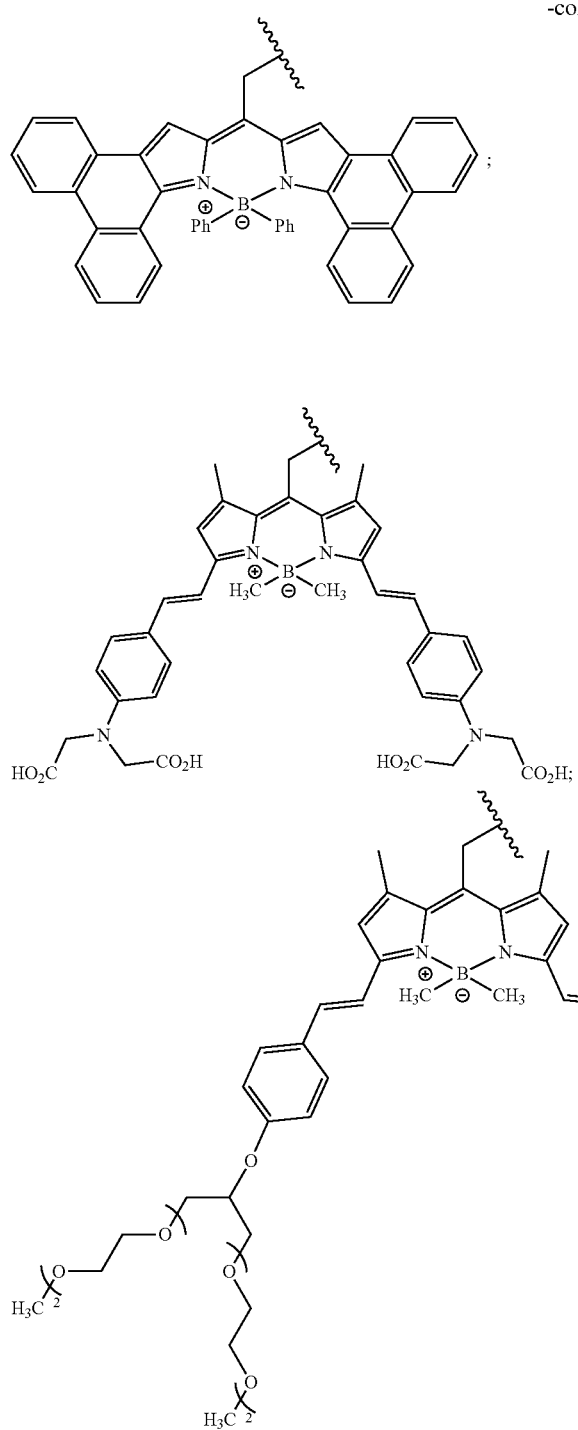
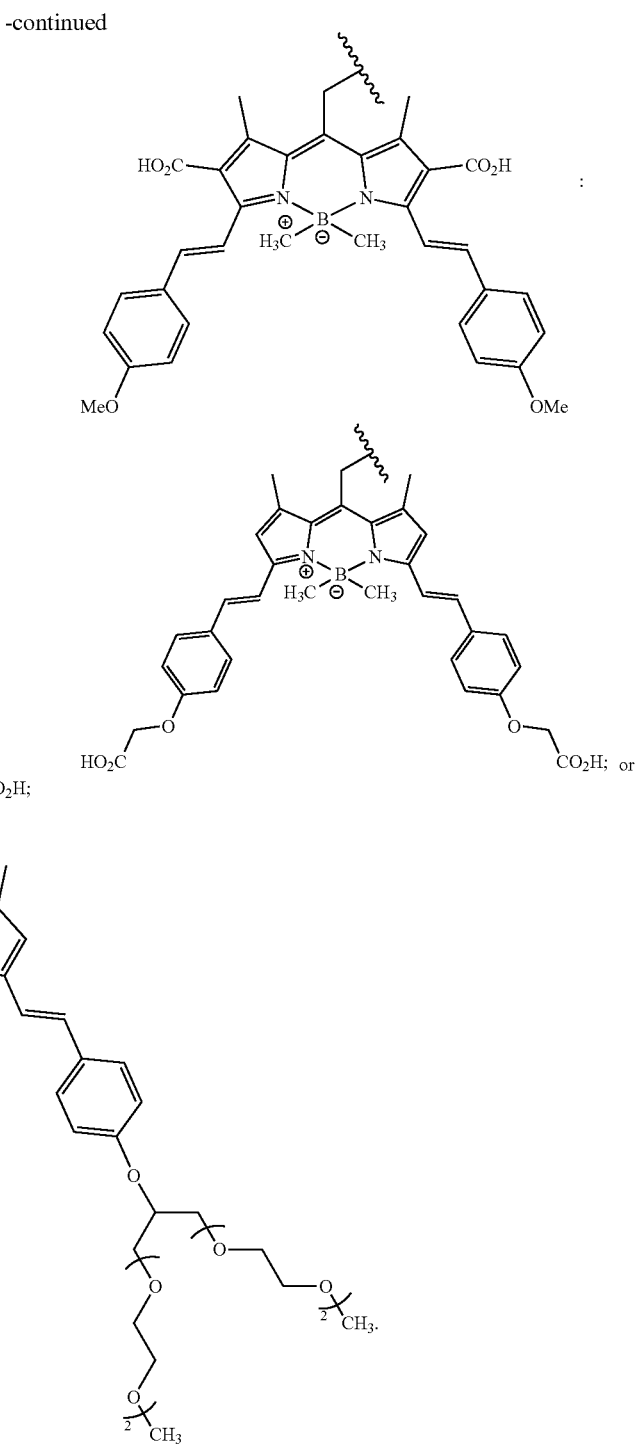

As mentioned herein, the moiety G in compounds of the formula A-G can be any organic or inorganic compound that can be photoreleasably linked directly or indirectly by any suitable means (e.g., covalently via ether, amine, ester, amide or carbamate linkages, or the like) to the moiety A. The various compounds, organic and inorganic, that are contemplated herein for the moiety G include, but are not limited to, the "caged" or "masked" portion of the compounds described in Petr Klán et al., *Chem. Rev.* 113: 119-191 (2013); Dynamic Studies in Biology 5-20 (Maurice Goeldner and Richard Givens eds., Wiley VCH Verlag GmbH & Co. KGaA 2005); and Haitao Yu el al., *Chem. Soc. Rev.* 39: 465-473 (2010); all of which are incorporated by reference as if fully set forth herein.

When the moiety G, or fragment thereof, is photoreleased via the various embodiments of the methods described herein, the moiety G can be in an ionic form, e.g., a carboxylate ($RCOO^-$); an $RO^-$ anion; an $RS^-$ anion; an $ROP(O)_2O^-$ anion; an $RP(O)_2O^-$ anion; an $R_2N^-$ anion; and the like, wherein R is an optionally substituted $C_1$-$C_6$-alkyl, optionally substituted $C_2$-$C_6$-alkenyl, optionally substituted $C_6$-$C_{14}$-aryl, ($C_6$-$C_{14}$-aryl)-($C_2$-$C_6$-alkenyl-), wherein the ($C_6$-$C_{14}$-aryl)-($C_2$-$C_6$-alkenyl-) is optionally substituted on the $C_2$-$C_6$-alkenyl or the $C_6$-$C_{14}$-aryl or optionally substituted ($C_2$-$C_8$-heterocyclyl-).

Examples of the moiety G include, but are not limited to, at least one of a protein, an oligopeptide, an amino acid, an oligonucleotide, an ion, and a small molecule. As used herein, the term "oligopeptide" refers to a molecule comprising 2 to 100 amino acid residues, e.g., 2 to 20 amino acid residues. As used herein, the term "oligonucleotide" refers to single-stranded nucleotide chain (as an oligodeoxynucleotide or oligoribonucleotide) comprising 2 to 100 nucleotides, e.g., 2 to 20 nucleotides.

Examples of proteins that may be comprised in the moiety G include, but are not limited to, caspases (e.g., caspase-3), phosphatases (e.g., protein tyrosine phosphatase), cholinesterases acetylcholinesterase and butyrylcholinesterase), esterases, transferases, restriction endonucleases (e.g. BamH1), hemoglobin, and the like.

Examples of ions include, but are not limited to, caged ions where the ion is caged within a chelating moiety, such as ethylenediamine tetraacetic acid (EDTA) and ethylene glycol tetraacetic acid (EGTA). Suitable ions include but are not limited to $Ca^{2+}$, $Mg^{2+}$, and the like. A non-limiting example of a compound of the formula A-G comprising a moiety G comprising a caged $Ca^{2+}$ is:

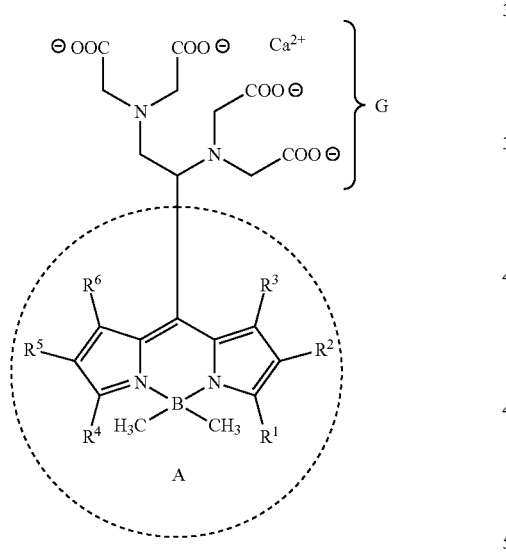

wherein the moiety A is depicted within the broken circle; and $R^1$, $R^2$, $R^3$, $R^4$, $R^5$, and $R^6$ are each, independently, hydrogen, halogen, optionally substituted $C_1$-$C_6$-alkyl, optionally substituted $C_2$-$C_6$-alkenyl or ($C_6$-$C_{14}$-aryl)-($C_2$-$C_6$-alkenyl-), wherein the ($C_6$-$C_{14}$-aryl)-($C_2$-$C_6$-alkenyl-) is optionally substituted on the $C_2$-$C_6$-alkenyl or the $C_6$-$C_{14}$-aryl. In this specific, non-limiting example, the moiety that is photoreleased is a fragment G' of the moiety G as show in Scheme I. In this instance, G' also includes the $Ca^{2+}$ ion.

While not wishing to be bound by any specific theory, it is believed that irradiating a composition comprising the compounds of the formula A-G described herein at a wavelength of >500 nm excites such compounds to their excited singlet state. It is believed that these compounds have excited singlet states with considerable diradical character. The excited singlet state undergoes heterolysis to generate an anion and a carbocation (carbocation not shown in Scheme I) that may be described as having ion diradical character rather than a closed-shell carbocation.

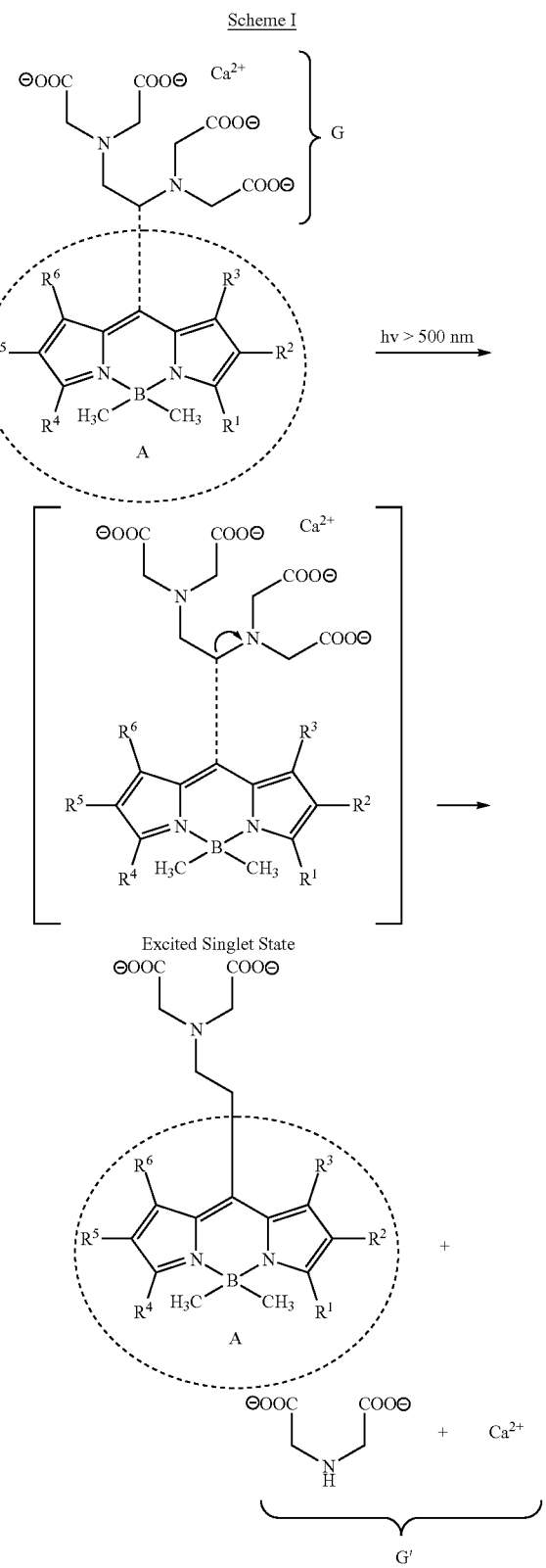

Scheme I

As used herein, the term "small molecule" comprised in the moiety G includes, but is not limited to a molecule having a molecular weight of less than 1000 g/mol. Examples of small molecules include, but are not limited to dyes, fragrances, nucleosides (e.g., adenosine, guanosine, uridine, cytidine, deoxyadenosine, deoxyguanosine, thymidine, deoxyuridine, and deoxycytidine), nucleotides (e.g., adenosine monophosphate, guanosine monophosphate, uridine monophosphate, cytidine monophosphate, deoxyadenosine monophospate, deoxyguanosine monophosphate, thymidine monophosphate, deoxyuridine monophosphate, and deoxycytidine monophosphate), neurotransmitters, pharmaceutical agents, and compounds involved in local immune responses, such as histamines. Nucleoside and nucleotide di- and triphosphates are also contemplated herein, including, but not limited to adenosine triphosphate (ATP) and guanosine triphosphate (GIP).

As used herein, the term "dye" includes any suitable dye including rhodamine-based dyes, fluorescein-based dyes, xanthene-based dyes, coumarins, cyanines, and boron dipyromethanes (BODIPYs). A non-limiting example of a compound of the formula A-G comprising a xanthene-based dye is:

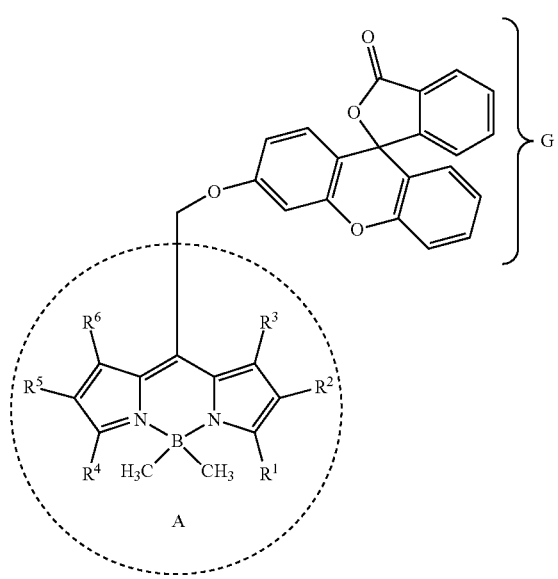

wherein the moiety A is depicted within the broken circle; and $R^1$, $R^2$, $R^3$, $R^4$, $R^5$, and $R^6$ are each, independently, hydrogen, halogen, optionally substituted $C_1$-$C_6$-alkyl, optionally substituted $C_2$-$C_6$-alkenyl or ($C_6$-$C_{14}$-aryl)-($C_2$-$C_6$-alkenyl-), wherein the ($C_6$-$C_{14}$-aryl)-($C_2$-$C_6$-alkenyl-) is optionally substituted on the $C_2$-$C_6$-alkenyl or the $C_6$-$C_{14}$-aryl. In this specific, non-limiting example, the moiety G that is photoreleased is shown in Scheme II:

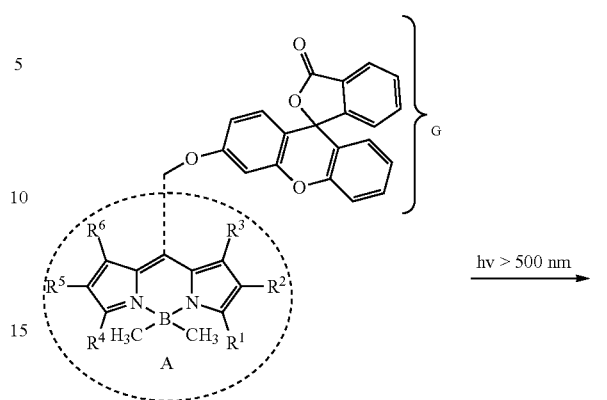

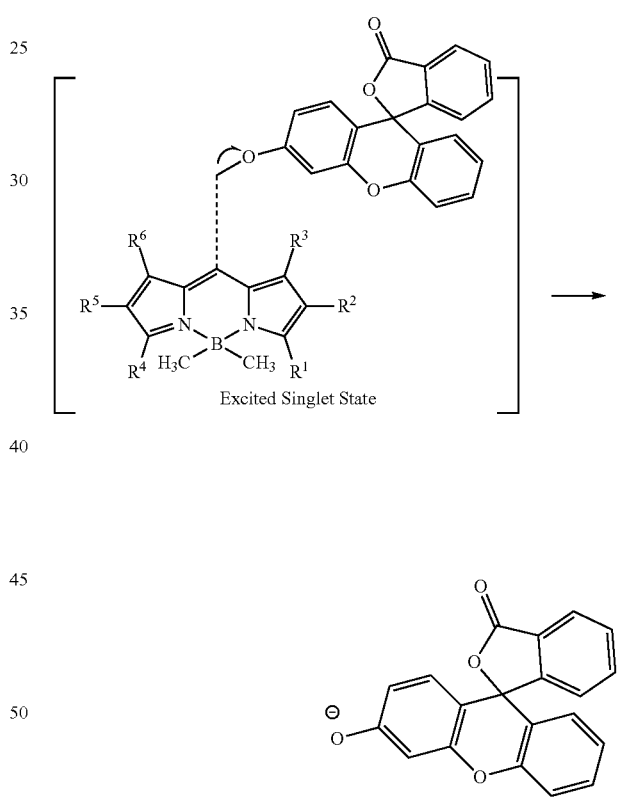

As used herein, the term fragrance includes, but is not limited to, terpene fragrances (e.g., damascone, geraniol, nerol, citronellol, linalool, and nerolidol or derivatives thereof), cyclic terpene fragrances (e.g., terpineol or derivatives thereof), aromatic fragrances (e.g., eugenol, vannilin, benzaldehyde, cinnamaldehyde, ethyl maltol, and thymol or derivatives thereof), and the like. In a specific, non-limiting example, the moiety G that is photoreleased is a damascone derivate, as shown in Scheme III:

Scheme III

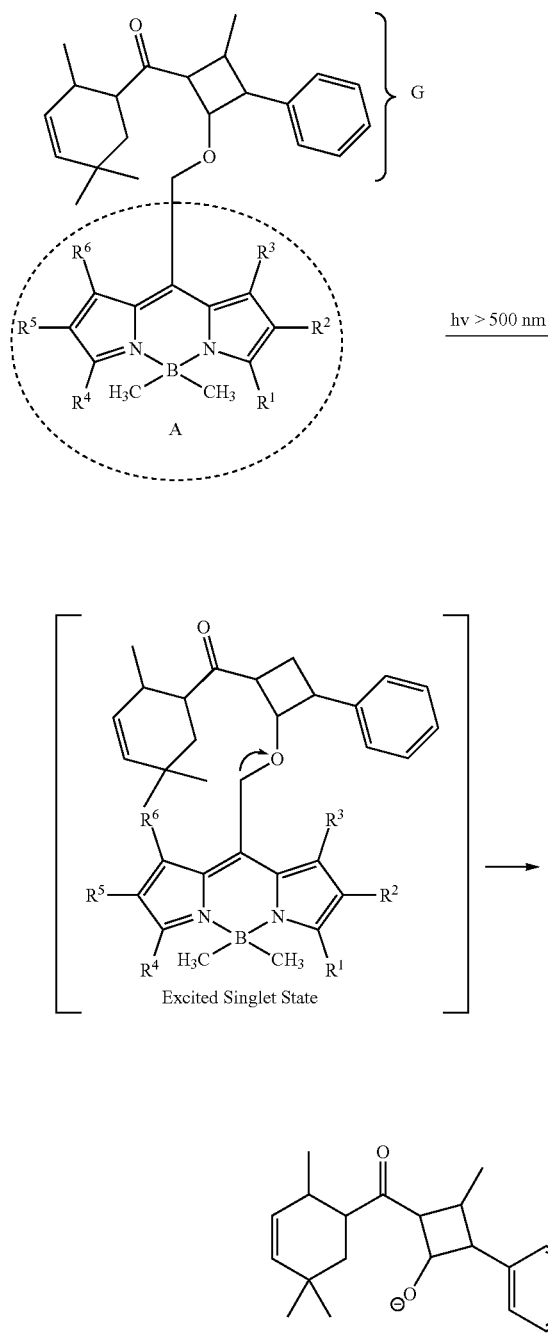

wherein the moiety A is depicted within the broken circle; and R¹, R², R³, R⁴, R⁵, and R⁶ are each, independently, hydrogen, halogen, optionally substituted $C_1$-$C_6$-alkyl, optionally substituted $C_2$-$C_6$-alkenyl or ($C_6$-$C_{14}$-aryl)-($C_2$-$C_6$-alkenyl-), wherein the ($C_6$-$C_{14}$-aryl)-($C_2$-$C_6$-alkenyl-) is optionally substituted on the $C_2$-$C_6$-alkenyl or the $C_6$-$C_{14}$-aryl.

As used herein, the term "neurotransmitter" includes, but is not limited to norepinephrine, glutamate, dopamine, gamma-aminobutyric acid, serotonin, and an endorphin. In a specific, non-limiting example, the moiety G that is photoreleased is glutamate, as shown in Scheme IV:

Scheme IV wherein the moiety A is depicted within the broken circle; and R¹, R², R³, R⁴, R⁵, and R⁶ are each, independently, hydrogen, halogen, optionally substituted $C_1$-$C_6$-alkyl, optionally substituted $C_2$-$C_6$-alkenyl or ($C_6$-$C_{14}$-aryl)-($C_2$-$C_6$-alkenyl-), wherein the ($C_6$-$C_{14}$-aryl)-($C_2$-$C_6$-alkenyl-) is optionally substituted on the $C_2$-$C_6$-alkenyl or the $C_6$-$C_{14}$-aryl.

In some embodiments, G is not acetate ($CH_3COO^-$).

As stated herein, the moieties A and G in compounds of the formula A-G can be photoreleasably linked directly or indirectly by any suitable means (e.g., covalently via ether, amine, ester, amide or carbamate linkages, or the like). Direct linkages between the moieties A and G are specifically exemplified in Schemes I-IV. In those specific cases, the moiety G is linked through a —$CH_2$—NH— linkage (Scheme I); through a —$CH_2$—O— linkage (Schemes II and III); and through a —$CH_2$—O—C(O)— linkage (Scheme IV); where the —NH— group; the —O— group; and the —O—C(O)— groups are part of the moiety G.

The moieties A and G in compounds of the formula A-G can also be photoreleasably linked indirectly via a linking group L in a compound of the formula A-$L_x$-G (wherein x is 0 or 1) where the linking group can be any suitable linking group including, but not limited to, acylalkylacyloxy (e.g., —O—C(O)($CH_2$)$_n$C(O)—, wherein n is an integer from 0 to 6); acylalkyloxy (e.g., —O—($CH_2$)$_n$C(O)—, wherein n is an integer from 0 to 6); (poly)alkylene glycol (e.g., [—O—

$(CH_2)_m$—O—$]_p$, wherein m is an integer from 1 to 3 and p is an integer from 1 to 20); aminoalkylamino (e.g., —$NR^7$—$(CH_2)$—$NR^7$—, wherein n is an integer from 0 to 6 and each $R^7$ is independently H or $C_1$-$C_6$-alkyl); aminoalkyloxy (e.g., —O—$(CH_2)_n$—$NR^7$—, wherein n is an integer from 0 to 6 and $R^7$ is H or $C_1$-$C_6$-alkyl); acylalkylamino (e.g., —$NR^7$—$(CH_2)_nC(O)$—, wherein n is an integer from 0 to 6 and $R^1$ is H or $C_1$-$C_6$-alkyl); and the like, wherein the "alkyl" in acylalkylacyloxy, acylalkyloxy, (poly)alkylene glycol, aminoalkylamino, aminoalkyloxy, and acylalkylamino is optionally substituted. Those of skill in the art will recognize that when x in a compound of the formula A-$L_x$-G is 1, the group that is photoreleased is L-G. Those of skill in the art will also recognize that the linking groups exemplified herein can link the moieties A and G in the direction shown or in the opposite direction. For example, when L is —O—$(CH_2)_n$—$NR^7$—, the compound of the formula A-L-G can be A-O—$(CH_2)_n$—$NR^7$-G or A-$NR^7$—$(CH_2)_n$—O-G.

The compounds of the formula A-G are thermally stable. As used herein, the term "thermally stable" refers to compounds where there is no substantial change in the $^1$H NMR spectrum of a compound of the formula A-G after boiling the compound in methanol for 1 hour in a foil-wrapped vessel.

The instant disclosure is also directed to methods that can include irradiating a composition (e.g., within a cell comprising a compound of the formula A-G; or a solution of a compound of the formula A-G in any suitable organic, preferably polar, solvent, such as acetonitrile or an alkanol including methanol, ethanol, and the like; an aqueous solvent; or combinations of an organic solvent and an aqueous solvent) comprising the compound of the formula A-G at a wavelength of >500 nm, so as to photorelease the moiety G, or fragment thereof, from the moiety A; wherein the moiety A comprises a chromophore and the moiety G, or fragment thereof, comprises an organic compound (e.g., at least one of a protein, an oligopeptide, an amino acid, an oligonucleotide, an ion, a small molecule, and the like). In some embodiments, the compound of the formula A-G has a wavelength absorption maximum, $\lambda_{max}$, between about 510 nm to about 1000 nm (e.g., between about 510 nm to about 550 nm; about 520 nm to about 650 nm; about 525 nm to about 675 nm; about 550 nm to about 650 nm; about 600 nm to about 700 nm; about 600 to about 800 nm; about 700 nm to about 900 nm; or about 600 nm to about 1000 nm).

Independent of a $\lambda_{max}$ between about 510 nm to about 1000 nm or in addition to having a $\lambda_{max}$ between about 510 nm to about 1000 nm, the compound of the formula A-G can have an extinction coefficient measured at the compound A-G $\lambda_{max}$, of from about $4.0 \times 10^4$ cm to about $8.0 \times 10^4$ $M^{-1}cm^{-1}$ (e.g., from about $4.5 \times 10^4$ $M^{-1}cm^{-1}$ to about $7.5 \times 10^4$ $M^{-1}cm^{-1}$; about $5.0 \times 10^4$ $M^{-1}cm^{-1}$ to about $8.0 \times 10^4$ $M^{-1}cm^{-1}$; about $5.5 \times 10^4$ $M^{-1}cm^{-1}$ to about $7.5 \times 10^4$ $M^{-1}cm^{-1}$; or about $6.0 \times 10^4$ $M^{-1}cm^{-1}$ to about $8.0 \times 10^4$ $M^{-1}cm^{-1}$).

The compounds and methods of the various embodiments of the present invention can be used to study, among other things, biological systems and how those systems react when the moiety G is, or a fragment thereof, is photoreleased from a compound of the formula A-G. For example, the compounds of the formula A-G can be used to probe neuronal circuits, neuronal integration, and synaptic plasticity when the moiety G comprises a neurotransmitter such as glutamate and gamma aminobutyric acid (GABA). See Dynamic Studies in Biology 212-247 (Maurice Goeldner and Richard Givens eds., Wiley VCH Verlag GmbH & Co. KGaA 2005), which is incorporated by reference as if fully set forth herein.

Values expressed in a range format should be interpreted in a flexible manner to include not only the numerical values explicitly recited as the limits of the range, but also to include all the individual numerical values or sub-ranges encompassed within that range as if each numerical value and sub-range were explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods described herein, the steps can be carried out in any order without departing from the principles of the invention, except when a temporal or operational sequence is explicitly recited. Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those of ordinary skill in the art, and that such modifications and variations are considered to be within the scope of this invention as defined by the appended claims.

EXAMPLES

The present invention can be better understood by reference to the following examples which are offered by way of illustration. The present invention is not limited to the examples given herein.

Materials and Methods

Materials.

The reagents and solvents of the highest purity available were used as purchased, or they were purified/dried using the standard methods when necessary. All glassware was oven-dried prior to use. Purification procedures were performed using silica gel columns, preparative thin-layer chromatography or recrystallization. Flash column chromatography was performed using silica gel Merck 60 (230-400 mesh).

Methods.

All manipulation with photosensitive samples were accomplished under the red light ($\lambda$>600 nm). In the spectroscopy measurements, the lowest possible intensity of incident light was used; the spectroscopic identity of the samples was confirmed after each measurement to ensure that no unwanted photodegradation processes occurred. All measurements were accomplished using fresh solutions prepared in the dark. $^1$H and $^{13}$C NMR spectra were obtained in CDCl$_3$ on 101, 125, 400 and 500 MHz spectrometers. $^1$H chemical shifts are reported in ppm relative to the tetramethylsilane signal (TMS, $\delta$=0.00 ppm), using the residual solvent signal as an internal reference. $^{13}$C NMR chemical shifts are reported in ppm relative to the CDCl$_3$ signal as an internal standard. IR spectra were recorded on an FTIR spectrophotometer. Mass spectra (MS) and high resolution mass spectra (HRMS) were recorded using an ESI and APCI techniques. Absorption spectra and the molar absorption coefficients were obtained on a UV-vis spectrometer with matched 1.0-cm quartz cells. Molar absorption coefficients were determined from the absorption spectra (the average values were obtained from three independent measurements with solutions of different concentrations. No dependence of the molar absorption coefficient on the solution concentration was observed in the range of 1×10−3−1×10−6 M. Fluorescence spectra were recorded on an automated luminescence spectrometer in 1.0 cm quartz fluorescence cuvettes at 25±1° C.; the sample concentration was set to keep the absorbance below 0.1 at $\lambda_{max}$; each sample was measured five times, and the spectra were averaged. Emission and excitation spectra are normalized; they were corrected using standard correction files. A nanosecond flash lamp (filled with H$_2$) was used to determine the fluorescence lifetimes. The data obtained were deconvolved from the measured decay curves of the sample and the instrumental response function. The quantum yields of fluorescence were obtained using a calibrated integration sphere.

The nanosecond laser flash photolysis (LFP) setup was operated in a right-angle arrangement of the pump and probe beams. Laser pulses of 170 ps duration at 532 nm ($E_{pulse}$=240 mJ) were obtained from a Nd:YAG laser. The laser beam was dispersed on a 40-mm long and 10-mm wide modified fluorescence cuvette (a 40-mm optical path). The probe light from a xenon lamp was filtered as necessary. The measurements were performed at ambient temperature (20±2° C.). Kinetic traces were fitted using the Levenberg-Marquard algorithm. All measurements were performed at least three times unless stated otherwise. All samples were irradiated by a single laser flash, and the cuvette was filled with a fresh solution after each measurement. If necessary, the samples were degassed by a freeze-pump-thaw technique (3 cycles).

Irradiation in the UV Cuvettes.

A solution of the given compound (3.0 mL) in a matched 1.0 cm quartz PTFE screw-cap fluorescence cuvette equipped with a stir bar was irradiated with a light source (32 LEDs emitting at the selected wavelength: $\lambda_{max}$=365, 490, 507 nm; the bandwidths at half height=30 nm; high-pressure 450 W mercury-xenon arc lamp with a monochromator with 200-1600 nm grating set to 365±0.5 nm). The reaction progress was monitored by UV-vis spectrometry using a diode-array spectrophotometer in a kinetic mode.

Quantum Yields.

Photodegradation quantum yields for both aerated and degassed (freeze-pump-thaw technique; 3 cycles) solutions in methanol were determined at $\lambda$irr=365 (LEDs and mercury-xenon arc lamp), 490 nm (LEDs), and 507 nm (LEDs) with xanthene-9-carboxylic acid1 and BODIPY-CORM2 as actinometers; most values were cross-checked using ferrioxalate3 at $\lambda$irr=365 nm. The data were processed using single value decomposition (SVD) software assuming the first-order rate law. The amount of absorbed light was calculated from the whole emission spectrum of the light source. The quantum yield of photodegradation was found to be independent on the concentration (in range from c=1× 10−2 to 1×10−6 M) and excitation wavelength (356 to 507 nm). All quantum yield measurements were repeated at least 6 times with independently prepared samples.

Stability of the Compounds in the Dark.

All compounds in methanol solutions (c=~1×10−4 mol dm-3) kept in the dark at 22° C. for at least 3 months were found to be chemically stable.

Quantum Yields of Intersystem Crossing.

The intersystem crossing quantum yields were calculated from the relative ratios of the areas of the absorption and ground state bleach bands in the transient spectra according to a published procedure.4,5 All spectra were obtained with fresh samples under the same experimental conditions, and the measurements were repeated at least six times. The absorbance of 0.1 at the excitation wavelength was kept to minimize the interference of the ground state absorption. The light-saturation conditions (quantitative excitation of molecules to its excited state) were kept for all measurements.

Example 1: 4,4'-Dimethyl-8-chloromethyl-1,3,5,7-tetramethyl-4-bora-3a,4a-diaza-s-indacene (1)

Prepared according to the general procedure for obtaining BODIPY chlorides, from compound 7 as shown below:

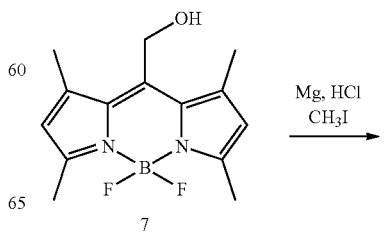

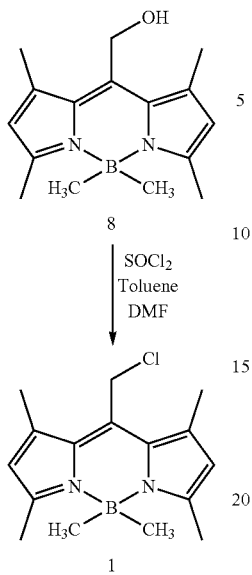

Compound 8 (60 mg, 0.2 mmol) and SOCl₂ (13.85 µL, 0.2 mmol in dry toluene (10 mL) and few drops of DMF; reaction time: 1 h. Compound 1 was purified by flash chromatography (hexane/ethyl acetate, 8:2). Orange solid. Yield 12 mg (20%). Mp. 197-201° C. ¹H NMR (400 MHz, CDCl₃) δ (ppm): 6.10 (s, 2H, 2CH), 4.86 (5, 2H, CH₂), 2.57 (s, 6H, 2CH₃), 2.47 (s, 6H, 2CH₃), 0.22 (s, 3H, CH₃), 0.16 (s, 3H, CH₃). ¹³C NMR (100 MHz, CDCl₃) δ (ppm): 153.34 (C), 136.89 (C), 136.31 (C), 129.97 (C), 122.87 (C), 38.24 (CH₃), 16.75 (CH₃), 16.07 (CH₃). HRMS-ESI m/z: [M]⁺ calcd for $C_{16}H_{22}BClN_2$ 288.1674, found 288.1671.

Example 2: 4,4'-Dimethyl-8-methyl(2-phenylacetate)-1,3,5,7-tetramethyl-4-bora-3a,4a-diaza-s-indacene (2)

Prepared according to the general procedure for esterification reaction, from compound 8 as shown below:

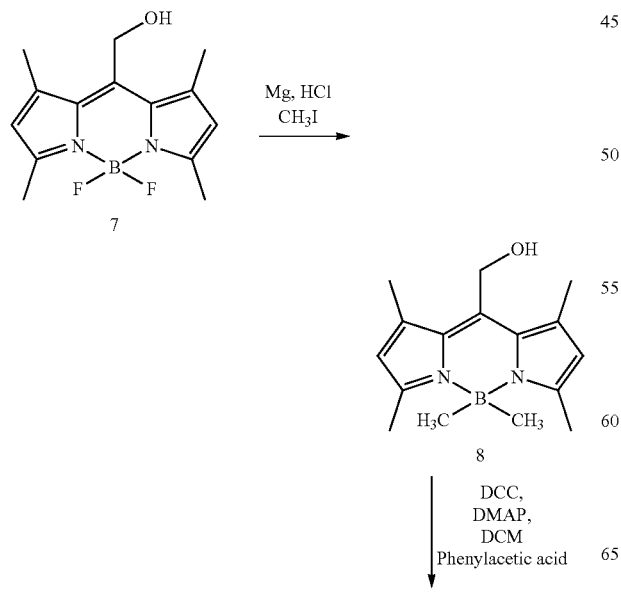

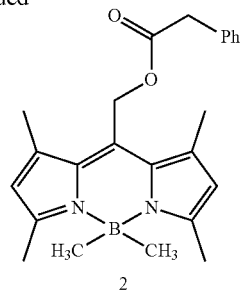

Compound 8 (69 mg, 0.23 mmol), phenylacetic acid (62 mg, 0.46 mmol), DCC (110 mg, 0.55 mmol) and ©MAP (3 mg, 0.023 mmol) in dry dichloromethane (10 mL); reaction time: 4 h. Compound 2 was purified by flash chromatography (dichloromethane). Dark orange crystals. Yield 60 mg (81%). Mp. 115-118° C. ¹H NMR (400 MHz, CDCl₃) δ 7.38-7.07 (m, 5H, 5CH), 6.02 (s, 2H, 2CH), 5.30 (s, 2H, CH₂), 3.65 (s, 2H, CH₂), 2.43 (s, 6H, 2CH₃), 2.20 (5, 6H, 2CH₃), 0.17 (s, 6H, 2CH₃). ¹³C NMR (100 MHz, CDCl₃) δ 171.55 (C), 153.31 (C), 137.25 (C), 133.57 (CH), 133.22 (C), 129.33 (CH), 128.79 (CH), 127.44 (C), 122.78 (CH), 59.21 (CH₂), 41.23 (CH₂), 16.72 (CH₃), 15.82 (CH₃), 15.79 (CH₃). HRMS-ESI m/z: [M]⁺ calcd for $C_{24}H_{29}BN_2O_2$ 388.2453, found 388.2422.

Example 3: 4,4'-Diethyl-8-methyl-(2-phenylacetate)-1,3,5,7-tetramethyl-4-bora-3a,4a-diaza-s-indacene (3)

Prepared according to the general procedure for esterification reaction from compound 9 (83.4 mg, 0.23 mmol), analogously to the synthesis of compound 2, compound 9:

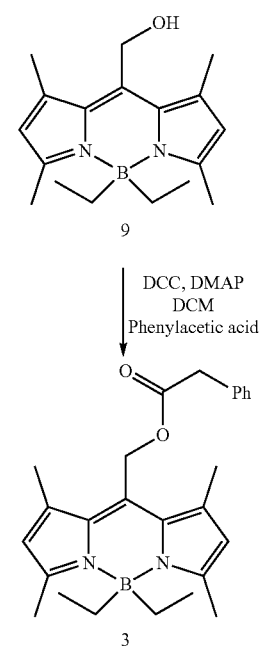

phenylacetic acid (62 mg, 0.46 mmol), DCC (110 mg, 0.55 mmol) and DMAP (3 mg, 0.023 mmol) in dry dichloromethane (10 mL); reaction time: 4 h. Purified by flash chromatography (dichloromethane). Dark orange crystals. Yield 69 mg (85%). Mp. 138-142° C. $^1$H NMR (400 MHz, CDCl$_3$) δ (ppm): 7.38-7.07 (m, 5H, 5CH), 6.05 (s, 2H,2CH), 5.34 (m, 2H, CH$_2$), 3.67 (s, 2H, CH$_2$), 2.44 (s, 6H, 2CH$_3$), 2.23 (s, 6H, 2CH$_3$), 0.79 (q, J=7.6 Hz, 4H, 2CH$_2$), 0.33 (t, J=7.6 Hz, 6H, 2CH$_3$). $^{13}$C NMR (100 MHz, CDCl$_3$) δ (ppm): 171.56 (C), 152.85 (CH), 136.84 (CH), 133.62 (C), 133.32 (C), 129.37 (CH), 128.76 (CH), 127.40 (C), 122.91 (CH), 59.28 (CH$_2$), 41.27 (CH$_2$), 16.68 (CH$_3$), 16.01 (CH$_3$), 9.24 (CH$_3$). HRMS-ESI m/z: [M]$^+$ calcd for C$_{26}$H$_{33}$BIN$_2$O$_2$ 416.2744, found 416.2735.

Example 4: 4,4'-Diphenyl-8-methyl-(2-phenylacetate)-1,3,5,7-tetramethyl-4-bora-3a,4a-diaza-s-indacene (4)

Prepared according to the general procedure for esterification reaction from compound 10 (80 mg, 0.2 mmol), analogously to the synthesis of compound 2, compound 10:

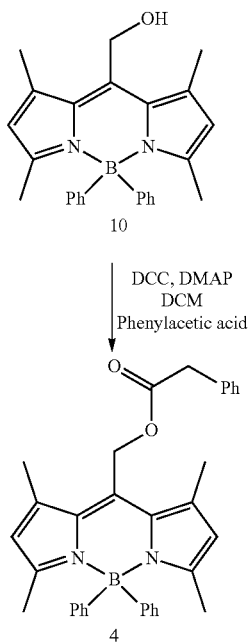

phenylacetic acid (54 mg, 0.4 mmol), DCC (96 mg, 0.48 mmol) and DMAP (3 mg, 0.02 mmol) in dry dichloromethane (10 mL); reaction time: 4 h. Compound 4 was purified by flash chromatography (dichloromethane). Orange solid. Yield 92 mg (90%). Mp. 140-144° C. $^1$H NMR (400 MHz, CDCl$_3$) δ (ppm): 7.41-7.18 (m, 15H, 15 CH), 6.05 (s, 2H, 2CH), 5.36 (s, 2H, CH$_2$), 3.75 (s, 2H, CH$_2$), 2.29 (s, 6H, 2CH$_3$), 1.80 (5, 6H, 2CH$_3$). $^{13}$C NMR (100 MHz, CDCl$_3$) δ (ppm): 171.40 (C), 155.84 (C), 138.76 (0), 133.67 (C), 133.63 (CH), 133.52 (C), 133.17 (C) 129.36 (CH), 128.80 (CH), 127.46 (CH), 127.40 (CH), 125.97 (CH), 123.12 (CH), 59.24 (CH$_2$), 41.25 (CH$_2$), 17.33 (CH$_3$), 15.64 (CH$_3$). HRMS-ESI m/z: [M]$^+$ calcd for C$_{34}$H$_{33}$BN$_2$O$_2$ 512.2744, found 512.2731.

Example 5: 2,6-Diiodo-4,4'-dimethyl-8-chloro ethyl-1,3,5,7-tetramethyl-4-bora-3a,4a-diaza-s-indacene (5)

Prepared according to the general procedure for obtaining BODIPY chlorides, from compound 11 as shown below:

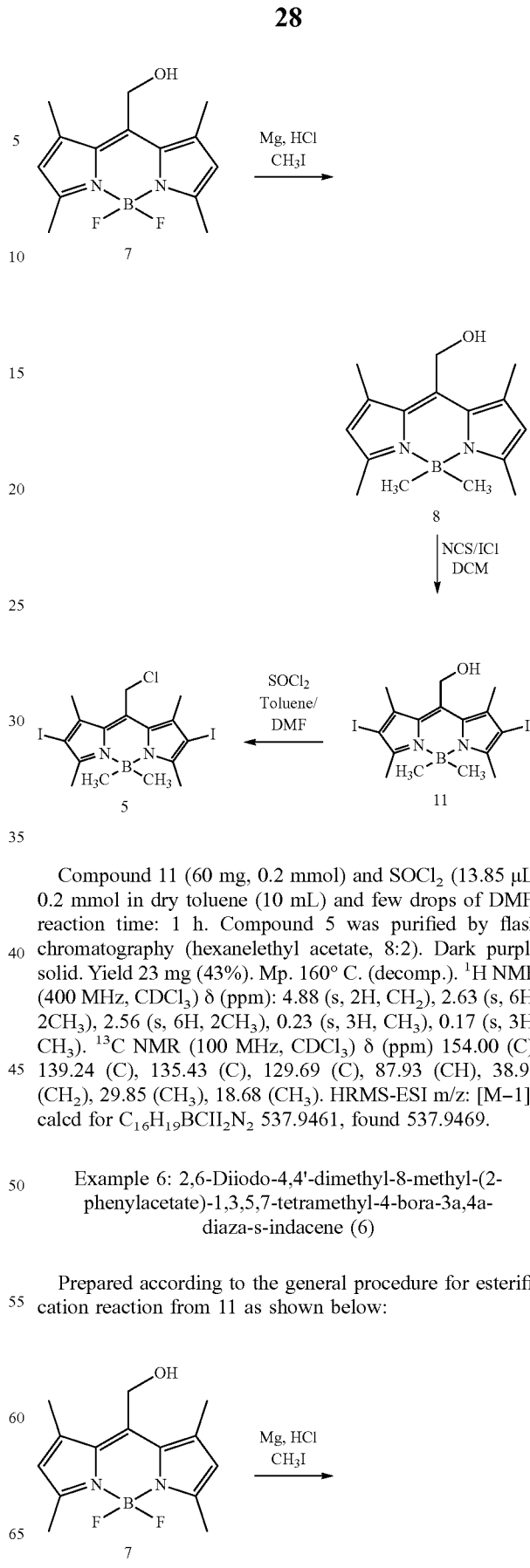

Compound 11 (60 mg, 0.2 mmol) and SOCl$_2$ (13.85 μL, 0.2 mmol in dry toluene (10 mL) and few drops of DMF; reaction time: 1 h. Compound 5 was purified by flash chromatography (hexanelethyl acetate, 8:2). Dark purple solid. Yield 23 mg (43%). Mp. 160° C. (decomp.). $^1$H NMR (400 MHz, CDCl$_3$) δ (ppm): 4.88 (s, 2H, CH$_2$), 2.63 (s, 6H, 2CH$_3$), 2.56 (s, 6H, 2CH$_3$), 0.23 (s, 3H, CH$_3$), 0.17 (s, 3H, CH$_3$). $^{13}$C NMR (100 MHz, CDCl$_3$) δ (ppm) 154.00 (C), 139.24 (C), 135.43 (C), 129.69 (C), 87.93 (CH), 38.96 (CH$_2$), 29.85 (CH$_3$), 18.68 (CH$_3$). HRMS-ESI m/z: [M–1]$^-$ calcd for C$_{16}$H$_{19}$BCII$_2$N$_2$ 537.9461, found 537.9469.

Example 6: 2,6-Diiodo-4,4'-dimethyl-8-methyl-(2-phenylacetate)-1,3,5,7-tetramethyl-4-bora-3a,4a-diaza-s-indacene (6)

Prepared according to the general procedure for esterification reaction from 11 as shown below:

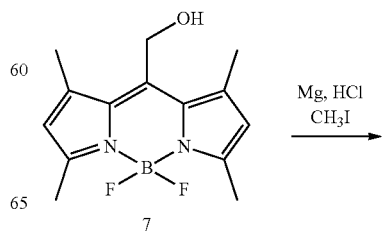

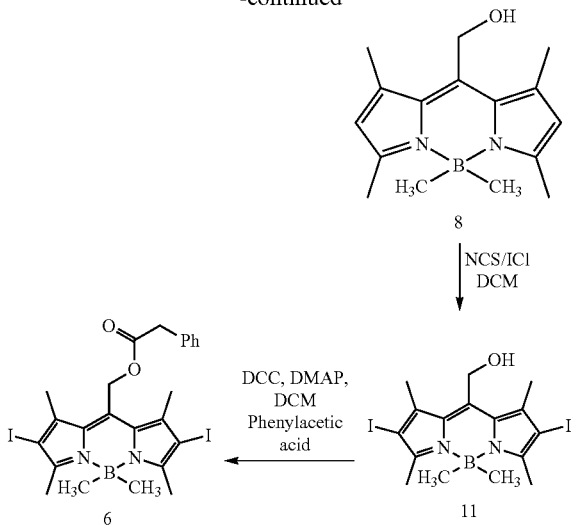

Compound 11 (49 mg, 0.08 mmol), phenylacetic acid (22 mg, 0.16 mmol), DCC (38 mg, 0.19 mmol) and DMAP (1 mg, 0.008 mmol) in dry dichloromethane (5 mL); reaction time: 4 h. Compound 6 was purified by flash chromatography (dichloromethane). Dark purple solid. Yield 36 mg (87%). Mp. 94-98° C. $^1$H NMR (400 MHz, CDCl$_3$) δ (ppm): 7.38-7.07 (m, 5H, 5CH), 5.35 (s, 2H, CH$_2$), 3.70 (s, 2H, CH$_2$), 2.55 (s, 6H, 2CH$_3$), 2.28 (s, 6H, 2CH$_3$), 0.21 (s, 6H, 2CH$_3$). $^{13}$C NMR (100 MHz, CDCl$_3$) δ (ppm): 171.34 (C), 153.94 (C), 139.60 (C), 133.31 (C), 132.52 (C), 131.16 (C), 129.31 (CH), 128.91 (CH), 127.63 (CH), 87.72 (CH), 59.62 (CH$_2$), 41.26 (CH$_2$), 18.57 (CH$_3$), 18.31 (CH$_3$). HRMS-ESI [M−1]$^-$ calcd for C$_{24}$H$_{26}$BI$_2$N$_2$O$_2$ 638.0218, found 638.0228.

Example 7

Compound 7, having the formula:

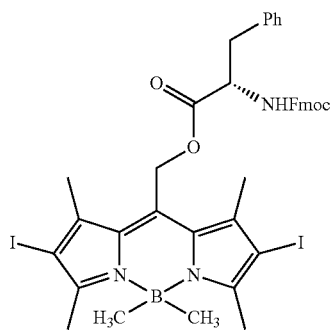

Can be synthesized using a procedure similar to the one described for compound 6, in Example 6, except that the phenylacetic acid is replaced with Fmoc-protected phenylalanine available from Sigma-Aldrich.

Example 8

The observed substrate release rate as a function of photolysis time is quantified by the quantum efficiency parameter (εφ), which is the product of the extinction coefficient at the irradiation wavelength (E) and the quantum yield (φ). Extinction coefficients for compounds 1-7 were determined by UV-Vis spectroscopy (see Table 1).

TABLE 1

Optical properties and quantum efficiencies of compounds 1-6

| Compound | $\lambda_{max}$ (nm) | $\lambda_{em}$ (nm) | ε | Φ | εΦ (M$^{-1}$cm$^{-1}$) |
|---|---|---|---|---|---|
| 1 | 519 | 556 | 60,580 | 0.68 | 41,194 |
| 2 | 512 | 550 | 68,500 | 0.11 | 7,398 |
| 3 | 513 | 550 | 55,300 | 0.08 | 4,424 |
| 4 | 517 | 562 | 58,300 | 0.01 | 583 |
| 5 | 542 | 573 | 62,400 | 0.95 | 59,280 |
| 6 | 538 | 572 | 60,700 | 0.28 | 16,996 |
| 7 | 537 | 573 | 63,000 | — | — |

What is claimed is:

1. A compound of the formula A-G or A-L-G, wherein:
G is an organic or inorganic compound photoreleasably linked to the moiety A, wherein G is photoreleasable from moiety A at wavelengths of >500 nm, wherein L, when present, is a linking group; and
A is of the formula I:

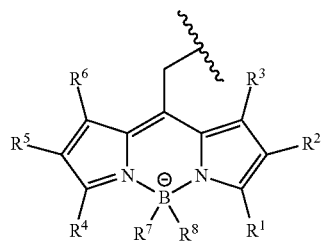

and salts thereof;
wherein:
the wavy line represents the attachment point of the moiety A to the moiety G or L-G at a heteroatom in G or L-G that is N, O, or Cl;
R$^1$, R$^2$, R$^3$, R$^4$, R$^5$, and R$^6$ are each, independently, hydrogen, optionally substituted C$_1$-C$_6$-alkyl, optionally substituted C$_2$-C$_6$-alkenyl or (C$_6$-C$_{14}$-aryl)-(C$_2$-C$_6$-alkenyl-), wherein the (C$_6$-C$_{14}$-aryl)-(C$_2$-C$_6$-alkenyl-) is optionally substituted on the C$_2$-C$_6$-alkenyl or the C$_6$-C$_{14}$-aryl; and
R$^7$ and R$^8$ are each, independently, optionally substituted C$_1$-C$_6$-alkyl, optionally substituted C$_2$-C$_6$-alkenyl or optionally substituted C$_6$-C$_{14}$-aryl; or
A is of formula II:

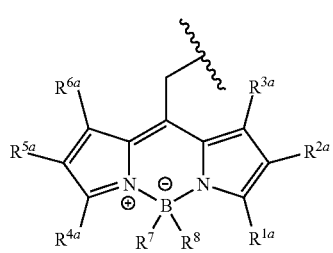

and salts thereof,
wherein:
the wavy line represents the attachment point of the moiety A to the moiety G or L-G at a heteroatom in G or L-G that is N, O, or Cl; $R^{1a}$, $R^{2a}$, $R^{3a}$, $R^{4a}$, $R^{5a}$, and $R^{6a}$ are each, independently, hydrogen, acyl, carboxy, optionally substituted $C_1$-$C_6$-alkyl, optionally substituted $C_1$-$C_6$-alkoxy, amino, optionally substituted $C_2$-$C_6$-alkenyl, optionally substituted $C_6$-$C_{14}$-aryl, optionally substituted $C_2$-$C_8$-heterocyclyl, or optionally substituted $C_2$-$C_8$-heterocyclyl-($C_2$-$C_6$-alkenyl-), wherein the ($C_2$-$C_8$-heterocyclyl)-($C_2$-$C_6$-alkenyl-) is optionally substituted on the $C_2$-$C_6$-alkenyl or the $C_2$-$C_8$-heterocyclyl, or $R^{1a}$ and $R^{2a}$, $R^{2a}$ and $R^{3a}$, $R^{4a}$ and $R^{5a}$ or $R^{5a}$ and $R^{6a}$, together with the carbon atoms to which they are attached, form an optionally substituted $C_2$-$C_8$-heterocyclyl or an optionally substituted $C_6$-$C_{14}$-aryl, and $R^7$ and $R^8$ are each, independently, optionally substituted $C_1$-$C_6$-alkyl, optionally substituted $C_2$-$C_6$-alkenyl or optionally substituted $C_6$-$C_{14}$-aryl.

2. The compound of claim 1, wherein A is of formula II, wherein $R^{1a}$ and $R^{4a}$ are each independently selected from an optionally substituted $C_1$-$C_6$-alkyl and an optionally substituted $C_2$-$C_6$-alkenyl.

3. The compound of claim 2, wherein A is of formula II, wherein $R^{1a}$ and $R^{4a}$ are each methyl or —CH═CH-Ph-4-OMe.

4. The compound of claim 1, wherein A is of formula II, wherein $R^{3a}$ and $R^{6a}$ are each, independently, an optionally substituted $C_1$-$C_6$-alkyl.

5. The compound of claim 4, wherein A is of formula II, wherein $R^{3a}$ and $R^{6a}$ are each methyl.

6. The compound of claim 1, wherein A is of formula II, wherein $R^{2a}$ and $R^{5a}$ are each hydrogen.

7. The compound of claim 1, wherein A is of formula II, wherein $R^7$ and $R^8$ are each, independently, methyl or phenyl.

8. The compound of claim 1, wherein A is of formula II, wherein at least one of $R^{1a}$, $R^{3a}$, $R^{4a}$, and $R^{6a}$ is $C_2$-$C_8$-heterocyclyl-($C_2$-$C_6$-alkenyl-).

9. The compound of claim 1, wherein A is of formula II, wherein at least one of $R^{1a}$ and $R^{4a}$ is $C_2$-$C_8$-heterocyclyl.

10. The compound of claim 1, wherein A is of formula II, wherein the moiety A is a moiety of the formula:

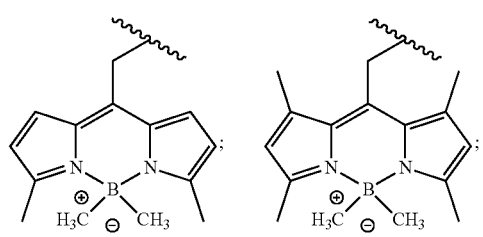

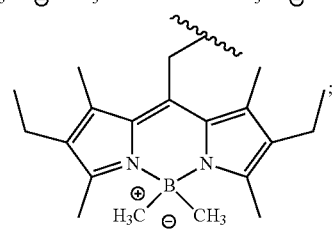

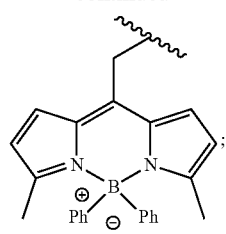

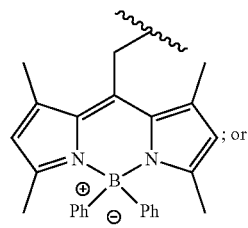

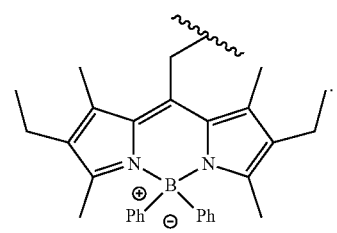

11. The compound of claim 1, wherein A is of formula II, wherein the moiety A is a moiety of the formula:

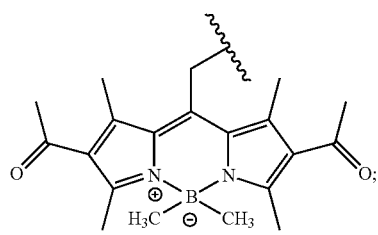

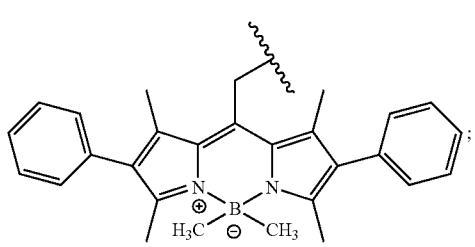

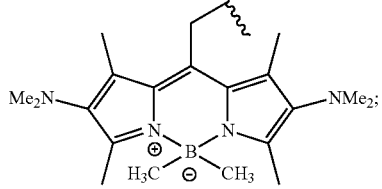

-continued
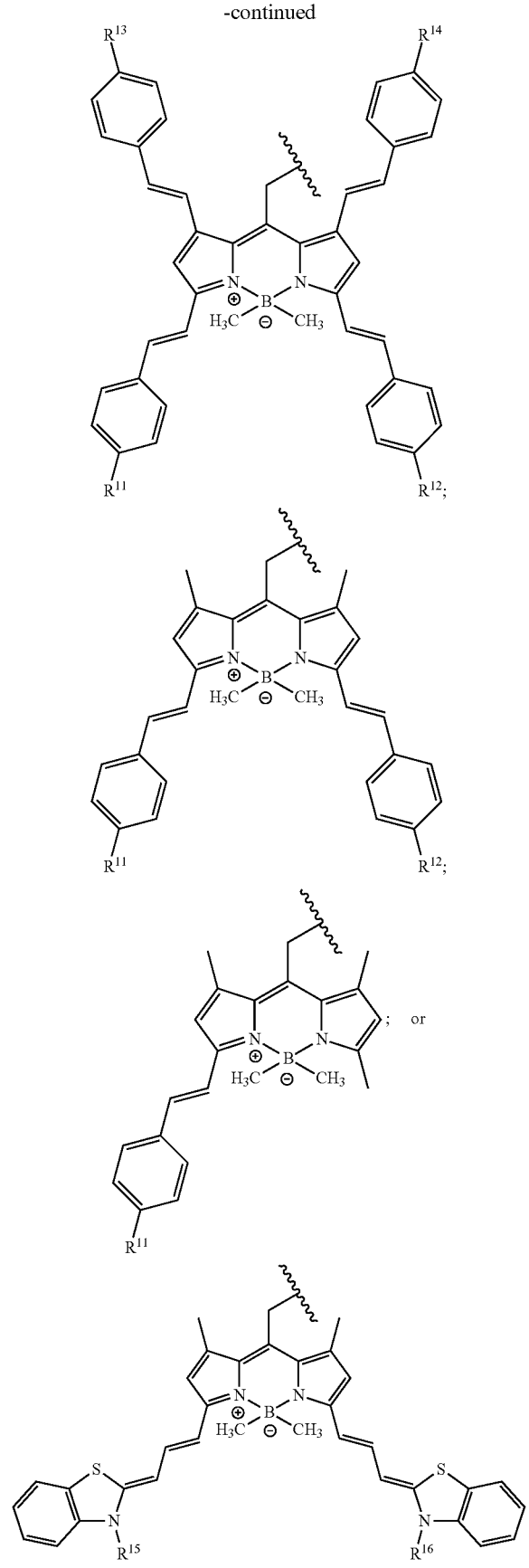
wherein $R^{11}$-$R^{14}$ are each independently H, halo, nitro, cyano, acyl, $C_1$-$C_6$-alkyl, $C_1$-$C_6$-alkoxy, amino or —[O—$R^9$-]$_p$O—$R^{10}$, wherein $R^9$ is alkylenyl or cycloalkylenyl, $R^{10}$ is alkyl, and p is an integer from 1 to 10; and $R^{15}$ and $R^{16}$ are each H or $C_1$-$C_6$-alkyl.
12. The compound of claim 1, wherein A is of formula II, wherein A is a moiety of formula:

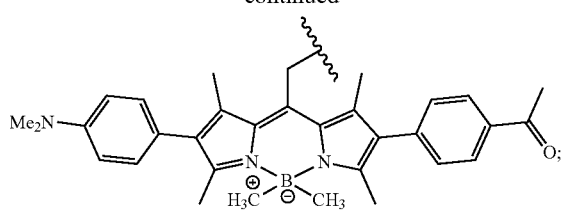
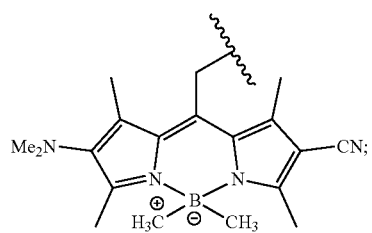
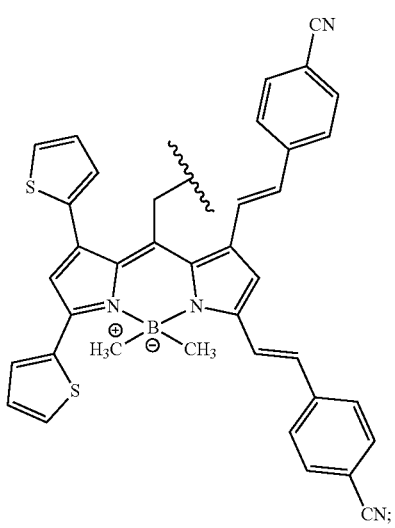
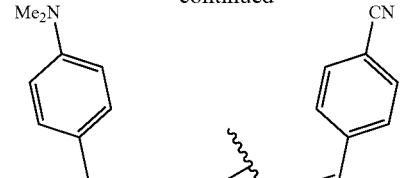
wherein $R^{15}$ is H or $C_1$-$C_6$-alkyl.
13. The compound of claim 1, wherein A is of formula II, wherein A is a moiety of formula:
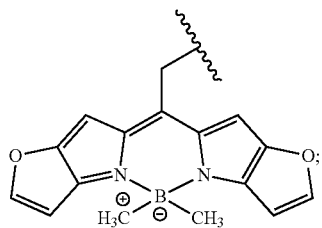
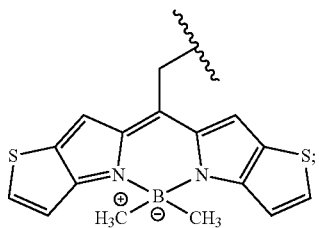
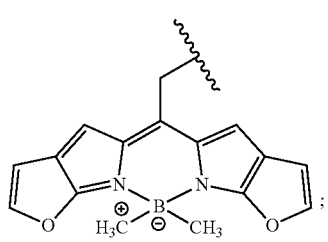
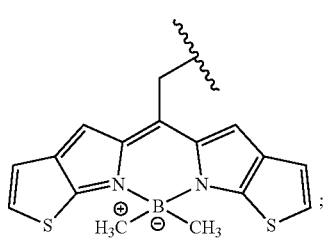

-continued
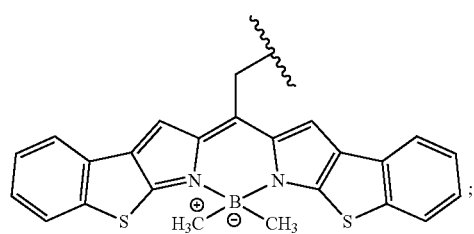
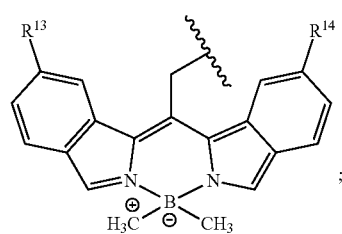
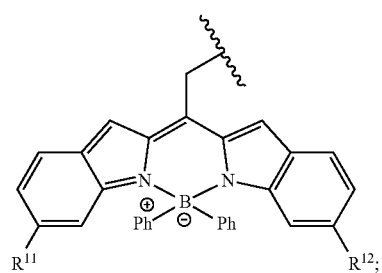
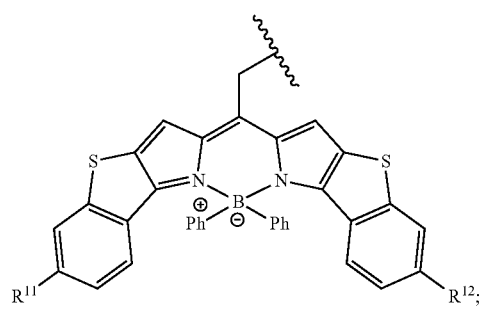
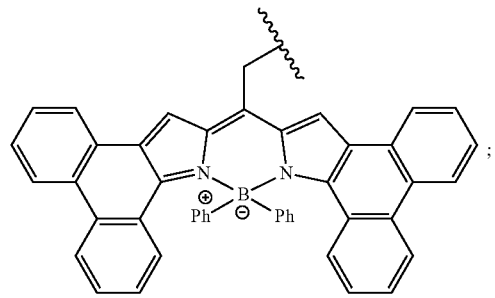
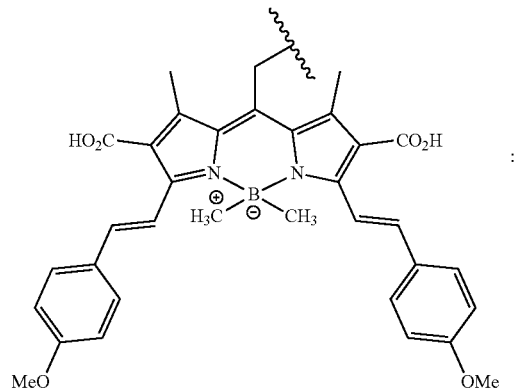
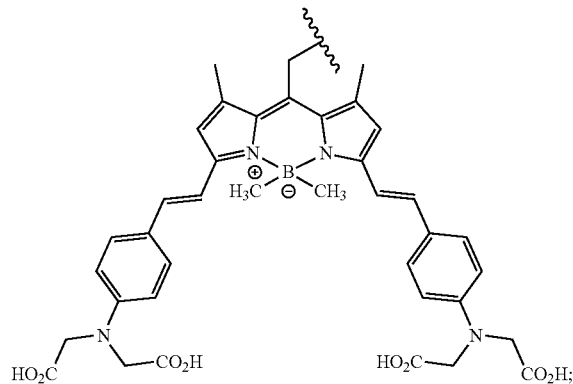
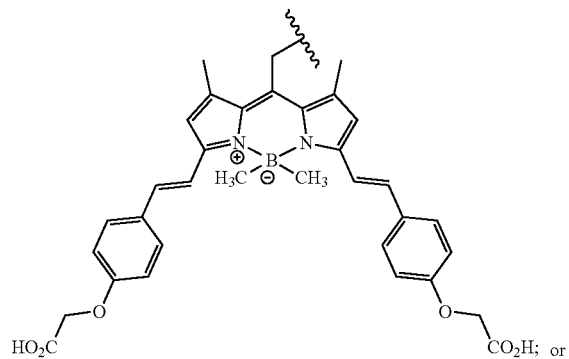 or -continued

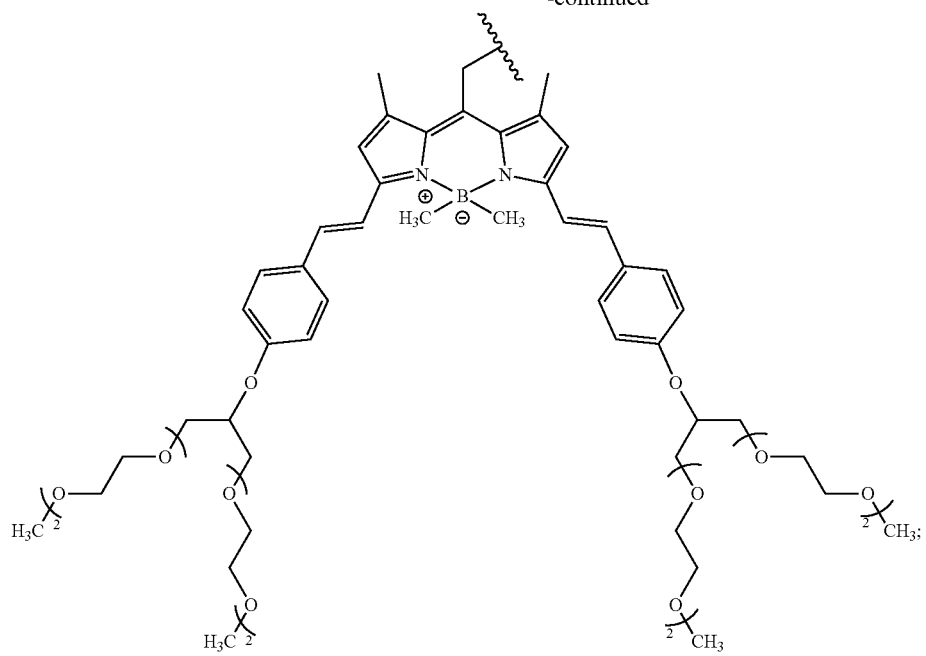

wherein $R^{11}$-$R^{14}$ are each independently H, halo, nitro, cyano, acyl, $C_1$-$C_6$-alkyl, $C_1$-$C_6$-alkoxy, amino or —[O—$R^9$-]$_p$O—$R^{10}$, wherein $R^9$ is alkylenyl or cycloalkylenyl, $R^{10}$ is alkyl, and p is an integer from 1 to 10; and $R^{15}$ and $R^{16}$ are each H or $C_1$-$C_6$-alkyl.

14. The compound of claim 1, wherein L is a linking group selected from the group consisting of acylalkylacyloxy, acylalkyloxy, (poly)alkylene glycol aminoalkylamino, aminoalkyloxy, and acylalkylamino, wherein the "alkyl" in acylalkylacyloxy, acylalkyloxy, (poly)alkylene glycol, aminoalkylamino, aminoalkyloxy, and acylalkylamino is optionally substituted.

15. The compound of claim 1, wherein the compound of the formula A-G or A-L-G has a wavelength absorption maximum, $\lambda_{max}$, between about 510 nm to about 1000 nm.

16. The compound of claim 1, wherein the compound of the formula A-G or A-L-G has an extinction coefficient measured at the compound of formula A-G $\lambda_{max}$ or the compound of formula A-L-G $\lambda_{max}$ of from about $4.0 \times 10^4$ $M^{-1}$ $cm^{-1}$ to about $8.0 \times 10^4$ $M^{-1}$ $cm^{-1}$.

17. The compound of claim 1, wherein the moiety G comprises at least one of a protein, an oligopeptide, an amino acid, an oligonucleotide, an ion, and a small molecule.

18. The compound of claim 17, wherein G comprises a protein and the protein comprised in the moiety G is selected from the group consisting of caspases, phosphatases, cholinesterases, esterases, transferases, restriction endonucleases, and hemoglobin.

19. The compound of claim 17, wherein the small molecule comprised in the moiety G is at least one of a dye, fragrance, nucleoside, nucleotide, neurotransmitter, and pharmaceutical agent.

20. The compound of claim 19, wherein G comprises a nucleoside and the nucleoside comprised in the moiety G is adenine, thymidine, cytosine, guanosine or uridine.

21. The compound of claim 19, wherein G comprises a nucleotide and the nucleotide comprised in the moiety G is adenosine triphosphate (ATP) or guanosine triphosphate (GTP).

22. The compound of claim 19, wherein G comprises a neurotransmitter and the neurotransmitter comprised in the moiety G is norepinephrine, glutamate, dopamine, gamma-aminobutyric acid, serotonin or an endorphin.

23. The compound of claim 1, wherein the moiety G is a moiety of the formula —O-G', wherein G' is at least one of a protein, an oligonucleotide, a polynucleotide, an ion, and a small molecule.

24. A method for photoreleasing a moiety G, or a fragment thereof, from a compound of the formula A-G of claim 1, comprising:
irradiating a composition comprising the compound of the formula A-G at a wavelength of >500 nm, so as to photorelease the moiety G, or a fragment thereof, from the moiety A.

25. A method for photoreleasing a moiety L-G, or a fragment thereof, from a compound of the formula A-L-G of claim 1, the method comprising:
irradiating a composition comprising the compound of the formula A-L-G at a wavelength of >500 nm, so as to photorelease the moiety L-G, or a fragment thereof, from the moiety A;
wherein the moiety L-G, or fragment thereof, comprises an organic compound.

26. A compound of the formula A-G or A-L-G, wherein:
G is an organic or inorganic compound photoreleasably linked to the moiety A, wherein G is photoreleasable from moiety A at wavelengths of >500 nm, wherein L, when present, is a linking group; and

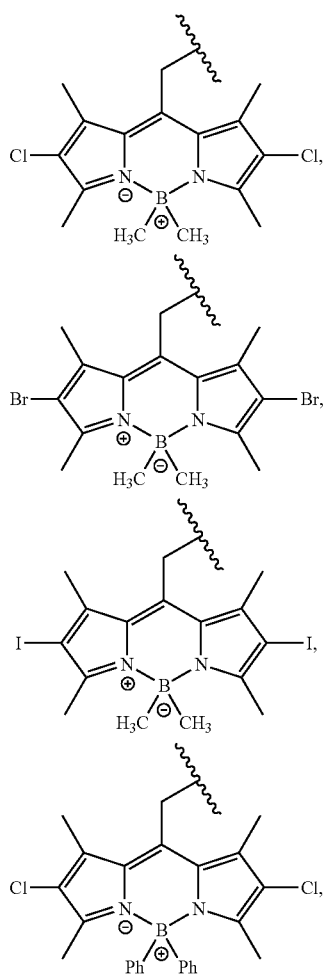
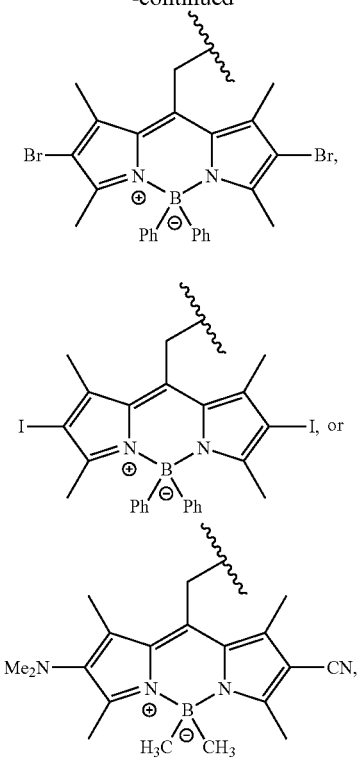
or salts thereof;
wherein:
the wavy line represents the attachment point of the moiety A to the moiety G or L-G at a heteroatom in G or L-G that is N, O, or Cl.
* * * * *

UNITED STATES PATENT AND TRADEMARK OFFICE
CERTIFICATE OF CORRECTION

PATENT NO. : 10,493,153 B2
APPLICATION NO. : 16/140218
DATED : December 3, 2019
INVENTOR(S) : Arthur Henry Winter It is certified that error appears in the above--identified patent and that said Letters Patent is hereby corrected as shown below:

In the Specification

In Column 2, Line 33, delete "($C_2$-$C_8$-alkenyl-)" and insert --($C_2$-$C_6$-alkenyl-)-- therefor In Column 2, Line 34, delete "$C_2$-$C_8$-alkenyl" and insert --$C_2$-$C_6$-alkenyl-- therefor In Column 2, Line 34, delete "$C_8$-$C_{14}$-aryl" and insert --$C_6$-$C_{14}$-aryl-- therefor In Column 2, Lines 36-37, delete "$C_1$-$C_8$-alkyl" and insert --$C_1$-$C_6$-alkyl-- therefor In Column 2, Line 37, delete "$C_8$-$C_{14}$-aryl." and insert --$C_6$-$C_{14}$-aryl.-- therefor In Column 2, Line 63, delete "$C_1$-$C_8$-alkyl," and insert --$C_1$-$C_6$-alkyl,-- therefor In Column 2, Line 64, delete "$C_1$-$C_8$-alkoxy," and insert --$C_1$-$C_6$-alkoxy,-- therefor In Column 2, Line 65, delete "$C_2$-$C_8$-alkenyl," and insert --$C_2$-$C_6$-alkenyl,-- therefor In Column 2, Line 65, delete "$C_8$-$C_{14}$-aryl," and insert --$C_6$-$C_{14}$-aryl,-- therefor In Column 2, Line 66, delete "$C_2$-$C_3$-heteracylyl," and insert --$C_2$-$C_8$-heterocylyl,-- therefor In Column 2, Line 67, delete "$C_2$-$C_3$-heterocycly-($C_2$-$C_8$-alkenyl-)," and insert --$C_2$-$C_8$-heterocycly-($C_2$-$C_6$-alkenyl-),-- therefor In Columns 2-3, Line 67 and Line 1, delete "($C_2$-$C_3$-heterocyclyl)-($C_2$-$C_8$-alkenyl-)" and insert --($C_2$-$C_8$-heterocyclyl)-($C_2$-$C_6$-alkenyl-)-- therefor In Column 3, Line 2, delete "$C_2$-$C_8$-alkenyl" and insert --$C_2$-$C_6$-alkenyl-- therefor Signed and Sealed this
First Day of December, 2020

Andrei Iancu
*Director of the United States Patent and Trademark Office*

CERTIFICATE OF CORRECTION (continued)
U.S. Pat. No. 10,493,153 B2

In Column 3, Line 6, delete "$C_8$-$C_{14}$-aryl:" and insert --$C_6$-$C_{14}$-aryl;-- therefor In Column 3, Line 7, delete "$C_1$-$C_8$-alkyl," and insert --$C_1$-$C_6$-alkyl,-- therefor In Column 3, Lines 7-8, delete "$C_2$-$C_8$-alkenyl" and insert --$C_2$-$C_6$-alkenyl-- therefor In Column 3, Line 8, delete "$C_8$-$C_{14}$-aryl." and insert --$C_6$-$C_{14}$-aryl.-- therefor In Column 3, Line 26, delete "pyrones;" and insert --pyrenes;-- therefor In Column 3, Lines 60-61, delete "cinnarnoyl," and insert --cinnamoyl,-- therefor In Column 4, Line 66, delete "$C_2$-$C_6$-heterocyclyl)" and insert --$C_2$-$C_8$-heterocyclyl)-- therefor In Column 5, Line 12, delete "$C_2$-$C_6$-heterocyclyl-." and insert --$C_2$-$C_8$-heterocyclyl-.-- therefor In Column 5, Line 53, delete "$R_{1a}$, $R_{3a}$, $R_{4a}$," and insert --$R^{1a}$, $R^{3a}$, $R^{4a}$,-- therefor In Column 5, Lines 53-54, delete "$C_2$-$C_3$-heteracycly-($C_2$-$C_6$-alkenyl-)." and insert --$C_2$-$C_8$-heterocycly-($C_2$-$C_6$-alkenyl-).-- therefor In Column 5, Line 67, delete "$R^8$" and insert --$R^6$-- therefor In Column 6, Line 17, delete "$R^1$" and insert --$R^7$-- therefor In Column 14, Line 59, delete "el" and insert --*et*-- therefor In Column 15, Line 19, before "acetylcholinesterase", insert --(e.g.,--

In Column 17, Line 22, delete "(GIP)." and insert --(GTP).-- therefor

In Column 19, Lines 25-41, delete " 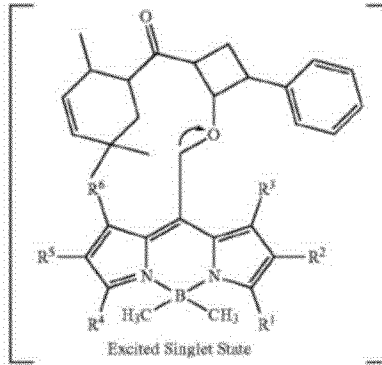 " and insert

CERTIFICATE OF CORRECTION (continued)
U.S. Pat. No. 10,493,153 B2

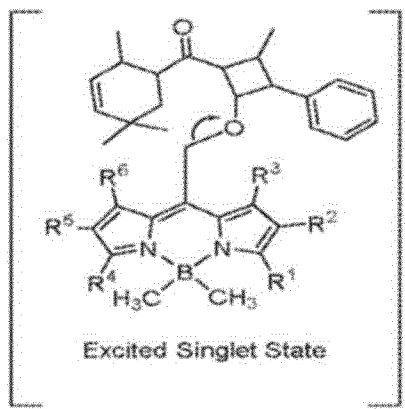

-- -- therefor

In Column 19, Line 65, delete "gamma-aminabutyric" and insert --gamma-aminobutyric-- therefor In Column 21, Line 7, delete "$R^1$" and insert --$R^7$-- therefor In Column 21, Line 49, delete "cm" and insert --$M^{-1}cm^{-1}$-- therefor In Column 23, Line 38, delete "1.0-cm" and insert --1.0 cm-- therefor In Column 23, Line 43, delete "1×10-3-1×10-6 M." and insert --$1\times10^{-3}$-$1\times10^{-6}$ M.-- therefor In Column 23, Line 60, delete "40-mm" and insert --40 mm-- therefor In Column 23, Line 60, delete "10-mm" and insert --10 mm-- therefor In Column 23, Line 61, delete "40-mm" and insert --40 mm-- therefor In Column 24, Line 21, delete "acidl" and insert --acid1-- therefor In Column 24, Lines 28-29, delete "c=1×10-2 to 1×10-6 M)" and insert --c=$1\times10^{-2}$ to $1\times10^{-6}$ M)-- therefor In Column 24, Lines 34-35, delete "(c=~1×10-4 mol dm-3)" and insert --(c=~$1\times10^{-4}$ mol dm-3)-- therefor In Column 25, Line 30, delete "(5," and insert --(s,-- therefor In Column 26, Line 15, delete "©MAP" and insert --DMAP-- therefor In Column 26, Line 21, delete "(5," and insert --(s,-- therefor In Column 26, Line 48, after "DMAP", insert --,--

In Column 27, Line 31, after "DMAP", insert --,--

CERTIFICATE OF CORRECTION (continued)
U.S. Pat. No. 10,493,153 B2

In Column 27, Line 50, delete "Hash" and insert --flash-- therefor

In Column 27, Line 54, delete "(5," and insert --(s,-- therefor

In Column 27, Line 55, delete "(0)," and insert --(C),-- therefor

In Column 27, Lines 62-63, delete "chloro ethyl" and insert --chloromethyl-- therefor In Column 28, Line 40, delete "(hexanelethyl" and insert --(hexane/ethyl-- therefor In Column 29, Line 34, after "HRMS-ESI", insert --*m/z*:-- therefor In Column 30, Line 1, delete "(E)" and insert --(ε)-- therefor In the Claims In Column 30, Lines 26-36, in Claim 1, delete " 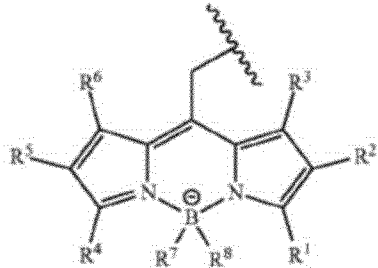 " and insert

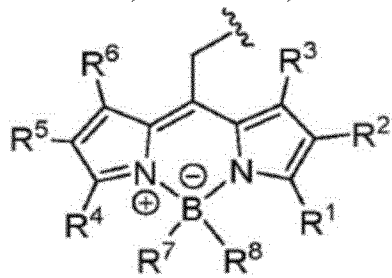

-- -- therefor

In Column 31, Lines 27-28, in Claim 3, delete "-CH-CH-Ph-4-OMe." and insert -- -CH=CH-Ph-4-OMe.-- therefor In Column 39, Line 39, in Claim 14, after "glycol", insert --,--

In Column 39, Line 55, in Claim 16, delete "$M^{-1}$ $cm^{-1}$" and insert --$M^{-1}cm^{-1}$-- therefor In Column 39, Line 55, in Claim 16, delete "$M^{-1}$ $cm^{-1}$." and insert --$M^{-1}cm^{-1}$.-- therefor In Column 40, Line 67, in Claim 26, after "and", insert --¶A is of the formula:--